United States Patent [19]
Klausener et al.

[11] Patent Number: 5,189,063
[45] Date of Patent: Feb. 23, 1993

[54] PESTICIDAL SUBSTITUTED ACRYLIC ESTERS

[75] Inventors: Alexander Klausener, Krefeld; Herbert Gayer, Monheim; Wolfgang Krämer, Burscheid; Dieter Berg, Wuppertal; Wilhelm Brandes, Leichlingen; Gerd Hänssler, Leverkusen; Ulrike Wachendorff-Neumann, Monheim, all of Fed. Rep. of Germany

[73] Assignee: Bayer Aktiengesellschaft, Leverkusen, Fed. Rep. of Germany

[21] Appl. No.: 570,099

[22] Filed: Aug. 17, 1990

[30] Foreign Application Priority Data

Sep. 1, 1989 [DE] Fed. Rep. of Germany ....... 3928999
May 10, 1990 [DE] Fed. Rep. of Germany ....... 4014940

[51] Int. Cl.$^5$ .................. A61K 31/22; C07C 69/76; C07C 321/24
[52] U.S. Cl. ........................... 514/530; 560/10; 560/15; 560/16; 560/20; 560/45; 560/47; 560/57; 560/58; 560/60
[58] Field of Search ................ 560/60, 10, 15, 16, 560/20, 22, 45, 47, 57, 58; 514/530

[56] References Cited

U.S. PATENT DOCUMENTS 4,723,034  2/1988  Schirmer et al. ............... 560/60
4,857,551  8/1989  Tapolczay et al. ............. 560/60

FOREIGN PATENT DOCUMENTS 0178826  10/1985  European Pat. Off.
0203606   5/1986  European Pat. Off.
0242081   3/1987  European Pat. Off.

Primary Examiner—Mukund J. Shah
Assistant Examiner—Y. N. Gupta
Attorney, Agent, or Firm—Sprung Horn Kramer & Woods

[57] ABSTRACT

Pesticidal substituted acrylic esters of the formula $$B=CH-C=C-\underset{\underset{CH-R^2}{\|}}{C}-COOR^1 \quad (I)$$

with substituents R, A, Q as shown in which
R$^1$ represents alkyl, or represents unsubstituted or substituted aralkyl,
R$^2$ represents dialkylamino, or represents a radical $-Z-R^3$,
R$^3$ represents alkyl, or represents unsubstituted or substituted aralkyl,
Z represents oxygen or sulphur,
A represents $$-(CH_2)_{\overline{n}},\ -CHR^4,\ -CR^4R^5\ \text{or}$$

where
n represents a number from 0 to 6,
R$^4$ and R$^5$ in each case independently of one another represent alkyl, or together represent an alkylene chain having 2 to 7 carbon atoms, and
R$^6$ represents alkyl, or represents a radical $$-\underset{\underset{O}{\|}}{C}-R^7$$

where
R$^7$ represents alkyl, alkoxy or dialkylamino,
B represents the group CH—R$^8$ or, where
R$^9$ represents unsubstituted or substituted alkyl, alkenyl, alkynyl, aralkyl, aryl or hetaryl, and
R and Q independently of one another represent hydrogen, alkyl, halogenoalkyl or alkoxy.

11 Claims, No Drawings

PESTICIDAL SUBSTITUTED ACRYLIC ESTERS

The invention relates to new substituted acrylic esters, to several processes for their preparation, to their use for combating pests, and to new intermediates.

It is known that certain substituted acrylic esters, such as, for example, the compound methyl 3-methoxy-2-(2-methylphenyl)-acrylate, have fungicidal properties (cf. for example EP 178,826).

New substituted acrylic esters have been found, of the general formula (I)

$$\underset{B=CH-C=C-\underset{\underset{CH-R^2}{\parallel}}{C}-COOR^1}{R\diagdown_{\diagup}^{A}\diagdown_{\diagup}^{Q}} \quad (I)$$

in which
- $R^1$ represents alkyl, or represents unsubstituted or substituted aralkyl,
- $R^2$ represents dialkylamino, or represents a radical $-Z-R^3$,
- $R^3$ represents alkyl, or represents unsubstituted or substituted aralkyl,
- Z represents oxygen or sulphur,
- A represents oxygen or sulphur, or represents one of the following groups $$-(CH_2)-_n, \quad -\underset{|}{C}HR^4, \quad -\underset{|}{C}R^4R^5 \text{ or } -\underset{|}{N}R^6,$$

where
- n represents a number from 0 to 6,
- $R^4$ and $R^5$ in each case independently of one another represent alkyl, or together represent an alkyl chain having 2 to 7 carbon atoms, and
- $R^6$ represents alkyl, or represents a radical $$-\underset{\underset{O}{\parallel}}{C}-R^7$$

where
- $R^7$ represents alkyl, alkoxy or dialkylamino,
- B represents the group $CH-R^8$ or $NO-R^9$,
where
- $R^8$ represents unsubstituted or substituted aryl or hetaryl and
- $R^9$ represents unsubstituted or substituted alkyl, alkenyl, alkynyl, aralkyl, aryl or hetaryl, and
- R and Q independently of one another represent hydrogen, alkyl, halogenoalkyl or alkoxy.

The compounds of the formula (I) can be in the form of geometric isomers or mixtures of isomers of various compositions. The invention claims the pure isomers as well as the isomer mixtures.

Furthermore, it has been found that the new substituted acrylic esters of the general formula (I)

$$\underset{B=CH-C=C-\underset{\underset{CH-R^2}{\parallel}}{C}-COOR^1}{R\diagdown_{\diagup}^{A}\diagdown_{\diagup}^{Q}} \quad (I)$$

in which
- $R^1$ represents alkyl, or represents unsubstituted or substituted aralkyl,
- $R^2$ represents dialkylamino, or represents a radical $-Z-R^3$,
- $R^3$ represents alkyl, or represents unsubstituted or substituted aralkyl,
- Z represents oxygen or sulphur,
- A represents oxygen or sulphur, or represents one of the following groups $$-(CH_2)-_n, \quad -\underset{|}{C}HR^4, \quad -\underset{|}{C}R^4R^5 \text{ or } -\underset{|}{N}R^6,$$

where
- n represents a number from 0 to 6,
- $R^4$ and $R^5$ in each case independently of one another represent alkyl, or together represent an alkyl chain having 2 to 7 carbon atoms, and
- $R^6$ represents alkyl, or represents a radical $$-\underset{\underset{O}{\parallel}}{C}-R^7$$

where
- $R^7$ represents alkyl, alkoxy or dialkylamino,
- B represents the group $CH-R^8$ or $NO-R^9$,
where
- $R^8$ represents unsubstituted or substituted aryl or hetaryl and
- $R^9$ represents unsubstituted or substituted alkyl, alkenyl, alkynyl, aralkyl, aryl or hetaryl, and
- R and Q independently of one another represent hydrogen, alkyl, halogenoalkyl or alkoxy, are obtained by one of the processes described below:

a) substituted acrylic esters of the formula (Ia)

$$\underset{B=CH-C=C-\underset{\underset{CH-OR^3}{\parallel}}{C}-COOR^1}{R\diagdown_{\diagup}^{A}\diagdown_{\diagup}^{Q}} \quad (Ia)$$

in which
$R^1$, $R^3$, A, B, R and Q have the abovementioned meanings,
are obtained when hydroxyacrylic esters or their alkali metal salts of the formula (II)

$$\underset{B=CH-C=C-\underset{\underset{CH-OM}{\parallel}}{C}-COOR^1}{R\diagdown_{\diagup}^{A}\diagdown_{\diagup}^{Q}} \quad (II)$$

in which

M represents hydrogen, or represents an alkali metal cation, and $R^1$, A, B, R and Q have the abovementioned meanings, are reacted with alkylating agents of the formula (III)

$$R^3-E^1 \qquad (III)$$

in which $E^1$ represents an electron-attracting leaving group and $R^3$ has the abovementioned meaning, if appropriate in the presence of a diluent and if appropriate in the presence of a reaction auxiliary;

b) substituted acrylic esters of the formula (Ib)

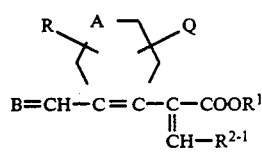
(Ib)

in which $R^{2-1}$ represents dialkylamino and $R^1$, A, B, R and Q have the abovementioned meanings, are obtained when substituted acetic esters of the formula (IV)

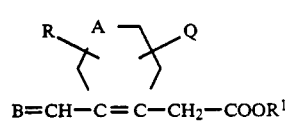
(IV)

in which $R^1$, A, B, R and Q have the abovementioned meanings, are reacted with formamides of the formula (Va)

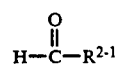
(Va)

in which $R^{2-1}$ has the abovementioned meaning, or with formamide derivatives of the formula (Vb)

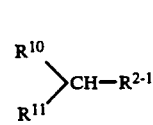
(Vb)

in which $R^{10}$ and $R^{11}$ independently of one another represent alkoxy or dialkylamino and $R^{2-1}$ has the abovementioned meaning, if appropriate in the presence of a diluent;

c) substituted acrylic esters of the formula (Ic)

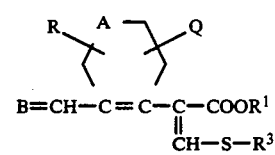
(Ic)

in which $R^1$, $R^3$, A, B, R and Q have the abovementioned meanings, are obtained when ketocarboxylic acid derivatives of the formula (VI)

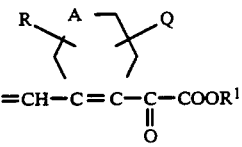
(VI)

in which $R^1$, A, B, R and Q have the abovementioned meanings, are reacted with organometallic compounds of the formula (VII)

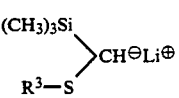
(VII)

in which $R^3$ has the abovementioned meaning, if appropriate in the presence of a diluent;

d) substituted acrylic esters of the formula (Ic) are furthermore obtained when substituted acrylic esters of the formula (VIII)

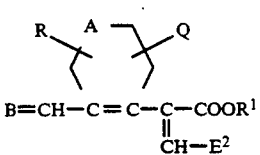
(VIII)

in which $R^1$, A, B, R and Q have the abovementioned meanings and $E^2$ represents an electron-attracting leaving group, are reacted with thiols of the formula (IX)

$$R^3-SH \qquad (IX)$$

in which $R^3$ has the abovementioned meaning, if appropriate in the presence of a diluent and if appropriate in the presence of a reaction auxiliary.

Finally, it has been found that the new substituted acrylic esters of the general formula (I) have a good action against pests.

Surprisingly, the substituted acrylic esters of the general formula (I) according to the invention show an insecticidal action and also a considerably more powerful fungicidal activity than the acrylic esters known from the prior art, such as, for example, the compound methyl 3-methoxy-2-(2-methylphenyl)-acrylate, which are compounds of a similar structure and a similar type of action.

Preferred substituents or ranges of the radicals listed in the formulae above and below follow:

Unsubstituted or substituted alkyl in the definitions of $R^1$, $R^3$, $R^4$, $R^5$, $R^6$, $R^7$, $R^8$, R and Q in the general formulae means straight-chain or branched alkyl preferably having 1 to 8, particularly preferably 1 to 6 and in particular 1 to 4, carbon atoms. The following may be mentioned as examples: unsubstituted or substituted methyl, ethyl, n-propyl, i-propyl, n-butyl, sec-butyl, i-butyl, t-butyl, n-pentyl, i-pentyl and t-pentyl.

The term unsubstituted or substituted alkenyl in the definitions of $R^9$ in the general formulae means straight-chain or branched alkenyl preferably having 2 to 8, particularly preferably 2 to 6 and in particular 2 to 4, especially preferably 3, carbon atoms. The following may be mentioned as examples: unsubstituted or substituted vinyl, allyl, prop-2-enyl, but-1-enyl, 2-butenyl, 3-butenyl and 1-methallyl.

Dialkylamino in the definition of $R^2$ and $R^7$ represents an amino group having 2 alkyl groups, each of which can be straight-chain or branched and identical or different, and each of which preferably contains 1 to 6, in particular 1 to 4, carbon atoms, methyl, ethyl, n- and i-propyl being mentioned. Examples which may be listed are dimethylamino, diethylamino, di-n-propylamino and di-i-propylamino.

The term unsubstituted or substituted aryl in the definition of $R^8$ and $R^9$ in the general formulae is understood as meaning aryl preferably having 6 to 10 carbon atoms in the aryl moiety. The following may be mentioned as preferred examples: unsubstituted or substituted phenyl or naphthyl, in particular phenyl.

Unsubstituted or substituted aralkyl in the definitions of $R^1$, $R^3$ and $R^9$ preferably contains 1 to 6, in particular 1 to 4, carbon atoms in the straight-chain or branched alkyl moiety, and preferably phenyl as the aryl moiety. Aralkyl groups which may be mentioned as preferred examples are benzyl and phenethyl.

Heteroaryl in the definition of $R^8$ and $R^9$ generally represents a 5- to 9-membered ring which contains one to 4, preferably 1 to 3, identical or different hetero atoms. Hetero atoms which may preferably be mentioned are oxygen, sulphur and nitrogen; the following may be mentioned as preferred examples: pyrimidinyl, pyrrolyl, isothiazolyl, oxazolyl, pyridyl, thienyl, furyl, pyridazinyl, pyrazinyl, isoxazolyl and thiazolyl.

The term unsubstituted or substituted alkynyl in the definition of $R^9$ in the general formulae is understood as meaning straight-chain or branched alkynyl having 2 to 8, preferably 2 to 6, in particular 2 to 4, particularly preferably 3, carbon atoms. Examples which may be mentioned are unsubstituted or substituted ethynyl, 3-propynyl, 2-butynyl, 3-butynyl and 1-methyl-2-propynyl.

Halogenoalkyl in the definitions R and Q represents straight-chain or branched radicals having in each case 1 to 4 carbon atoms, particularly preferably 1 or 2 carbon atoms, and in each case 1 to 9, preferably 1 to 5, identical or different halogen atoms as defined under halogen; the following may be mentioned as preferred examples: fluoromethyl, chloromethyl, bromomethyl, fluoroethyl, chloroethyl, bromoethyl, fluoro-n-propyl, chloro-n-propyl, difluoromethyl, trifluoromethyl, dichloromethyl, trichloromethyl, difluoroethyl, trifluoroethyl, trichloroethyl, chloro-difluoro-methyl, trifluorochloroethyl, chlorobutyl and fluorobutyl.

The unsubstituted or substituted alkoxy in the definition of $R^7$, R and Q in the general formulae is understood as meaning straight-chain or branched alkoxy preferably having 1 to 6, in particular 1 to 4, carbon atoms. Examples which may be mentioned are unsubstituted or substituted methoxy, ethoxy, propoxy and butoxy as well as their isomers, i-propoxy, i-, s- and t-butoxy.

The substituents of the aryl radicals as such or in compositions, such as arylalkyl, aryloxy, arylthio or aralkyloxy, and of the heterocyclic rings, such as heteroarylalkyl and heteroaryl, have the meanings given below.

Halogen as substituent generally represents fluorine, chlorine, bromine and iodine, preferably fluorine, chlorine and bromine, particularly preferably fluorine and chlorine.

Alkyl as substituent or in compositions, such as alkoximinoalkyl, generally represents straight-chain or branched alkyl, preferably having 1 to 6, -particularly preferably having 1 to 4, carbon atoms, and methyl, ethyl and t-butyl are especially preferred. The enumeration by way of example corresponds to that given further above.

Alkoxy as a substituent or in compositions, such as alkoximinoalkyl, generally represents straight-chain or branched alkoxy having 1 to 6, particularly preferably 1 to 3, carbon atoms per alkyl radical; the following may be mentioned as preferred examples: methoxy, ethoxy, n-and i-propoxy, n-, i-, s- and t-butoxy, n-hexoxy and i-hexoxy.

Alkylthio as a substituent in the radicals generally represents straight-chain or branched alkylthio preferably having 1 to 6 carbon atoms, for example it is taken to mean the following groups: methylthio, ethylthio, propylthio, butylthio and pentylthio, and their isomers, such as, for example, i-propylthio, i-, s- and t-butylthio, 1-methyl-butylthio, 2-methyl-butylthio- and 3-methyl-butylthio. Preferred alkylthio radicals contain 1 to 4 carbon atoms. Methylthio, ethylthio, n-, i-, s-propylthio and n-, i-, s- and t-butylthio are particularly preferred.

Halogenoalkyl and halogenoalkoxy as substituents in the radicals generally represent straight-chain or branched halogenoalkyl or halogenoalkoxy, in each case having 1 to 4 carbon atoms, particularly preferably having 1 or 2 carbon atoms, and in each case 1 to 9, preferably 1 to 5, identical or different halogen atoms as defined under halogen; the following may be mentioned as examples: fluoromethyl, chloromethyl, bromoethyl, fluoroethyl, chloroethyl, bromoethyl, fluoro-n-propyl, chloro-n-propyl, difluoromethyl, trifluoromethyl, dichloromethyl, trichloromethyl, difluoroethyl, trifluoroethyl, trichloroethyl, chloro-difluoro-methyl, trifluoroethyl, trichloroethyl, chlorobutyl, fluorobutyl, fluoromethoxy, chloromethoxy, bromomethoxy, fluoroethoxy, chloroethoxy, bromoethoxy, fluoropropoxy chloropropoxy, bromopropoxy, fluorobutoxy, chlorobutoxy, fluoro-i-propoxy, chloro-i-propoxy, difluoromethoxy, trifluoromethoxy, dichloromethoxy, trichloromethoxy, difluoroethoxy, trifluoroethoxy, tetrafluoroethoxy, trichloroethoxy, chlorodifluoromethoxy and trifluorochloroethoxy.

Halogenoalkylthio as a substituent in the radicals generally represents straight-chain or branched halogenoalkylthio, in each case having 1 to 4 carbon atoms, particularly preferably having 1 or 2 carbon atoms, and in each case having 1 to 9, preferably 1 to 5, identical or different halogen atoms as defined under halogen; the following may be mentioned as examples: fluoromethylthio, chloromethylthio, bromomethylthio, fluoroethylthio, chloroethylthio, bromoethylthio, fluoropropylthio, chloropropylthio, bromopropylthio, fluorobutylthio, chlorobutylthio, bromobutylthio, fluoro-i-propylthio, chloro-i-propylthio, difluoromethylthio, trifluoromethylthio, dichloromethylthio, trichloromethylthio, difluoroethylthio, trifluoroethylthio, tetrafluoroethylthio, trichloroethylthio, chlorodifluoromethylthio and trifluorochloroethylthio.

Alkoxycarbonyl as a substituent in the radicals in general represents straight-chain or branched alkoxycarbonyl having 1 to 4, preferably 1 or 2, carbon atoms in the alkoxy radical; the following may be mentioned as examples: methoxycarbonyl, ethoxycarbonyl, n-propoxycarbonyl, i-propoxycarbonyl, n-, i-, s- and t-butoxycarbonyl.

Cycloalkyl as a substituent in the radicals generally represents cycloalkyl preferably having 3 to 7, in particular 3, 5 or 6, carbon atoms. The following may be mentioned as examples: unsubstituted or substituted cyclopropyl, cyclobutyl, cyclopentyl, cyclohexyl and cycloheptyl.

Unsubstituted or substituted aryl, aryloxy and arylthio as substituents in the definition of $R^8$ and $R^9$ in the general formulae generally represent preferably having 6 to 10 carbon atoms in the aryl moiety. The following may be mentioned as examples: unsubstituted or substituted phenyl or naphthyl, phenoxy or phenylthio, in particular phenyl.

Unsubstituted or substituted aralkyl, aralkyloxy or aralkylthio as substituents in the definitions of $R^8$ and $R^9$ generally preferably contain 1 to 6 carbon atoms in the straight-chain or branched alkyl moiety and preferably phenyl as the aryl moiety. Aralkyl groups which may be mentioned as examples are benzyl, phenethyl, benzyloxy and benzylthio.

Heteroaryl, heteroaryloxy and heteroarylthio in the definition of $R^8$ and $R^9$ generally represent substituents of a 5- to 9-membered ring which contains one or more heteroatoms, preferably 1 to 3 identical or different heteroatoms. Heteroatoms which may be mentioned as preferred are oxygen, sulphur and nitrogen; the following may be mentioned as examples: pyridyl, thienyl, furyl, pyridazinyl, pyrazinyl, isoxazolyl and thiazolyl.

Formula (I) provides a general definition of the substituted acrylic esters according to the invention. Preferred compounds of the formula (I) are those in which $R^1$ represents straight-chain or branched alkyl having 1 to 6 carbon atoms, or represents aralkyl which has 1 to 4 carbon atoms in the straight-chain or branched alkyl moiety and 6 to 10 carbon atom in the aryl moiety and which is unsubstituted or monosubstituted or polysubstituted in the aryl moiety by identical or different substituents, suitable aryl substituents being those mentioned in the case of $R^8$, $R^2$ represents dialkylamino having 1 to 6 carbon atoms in each of the individual straight-chain or branched alkyl moieties, or represents a radical $-Z-R^3$,
where
$R^3$ represents straight-chain or branched alkyl having 1 to 6 carbon atoms, or represents aralkyl which has 1 to 4 carbon atoms in the straight-chain or branched alkyl moiety and 6 to 10 carbon atoms in the aryl moiety and which is unsubstituted or monosubstituted or polysubstituted in the aryl moiety by identical or different substituents, suitable aryl substituents being those mentioned in the case of $R^8$, Z represents oxygen or sulphur, A represents oxygen or sulphur, or represents one of the following groups $-(CH_2)-_n, -CHR^4, -CR^4R^5$ or $-NR^6$ where
n represents a number from 0 to 3,
$R^4$ and $R^5$ in each case independently of one another represent straight-chain or branched alkyl having 1 to 6 carbon atoms, or together represent an alkyl chain having 2 to 7 carbon atoms, and
$R^6$ represents straight-chain or branched alkyl having 1 to 6 carbon atoms, or represents a radical

where
$R^7$ represents straight-chain or branched alkyl having 1 to 6 carbon atoms, straight-chain or branched alkoxy having 1 to 6 carbon atoms, or straight-chain or branched dialkylamino having 1 to 6 carbon atoms in each of the individual alkyl moieties, B represents the group $CH-R^8$ or $NO-R^9$,
where
$R^8$ represents unsubstituted or substituted aryl having 6 to 10 carbon atoms in the aryl moiety, or represents heteroaryl having 2 to 9 carbon atoms and 1 to 4 identical or different hetero atoms—in particular nitrogen, oxygen and/or sulphur—in the heteroaryl moiety, suitable aryl and heteroaryl substituents in each case being: halogen, cyano, nitro, in each case straight-chain or branched alkyl, alkoxy or alkylthio, each of which has 1 to 4 carbon atoms, alkylidenedioxy having 1 to 6 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, cycloalkyl having 3 to 7 carbon atoms, divalent alkanediyl having 3 to 5 carbon atoms, or aryl, aralkyl, aryloxy, arylthio, aralkyloxy or aralkylthio, each of which has 6 to 10 carbon atoms in the aryl moiety and where appropriate 1 to 4 carbon atoms in the straight-chain or branched alkyl moiety and each of which is optionally monosubstituted or polysubstituted in the aryl moiety by identical or different substituents from the series comprising halogen, alkyl, alkoxy, alkylthio, halogenoalkyl, halogenoalkoxy or halogenoalkylthio, each of which has 1 to 4 carbon atoms and if appropriate 1 to 9 identical or different halogen atoms, or represents heteroarylalkyl, heteroaryloxy, heteroarylthio or heteroaryl, each of which has 2 to 9 carbon atoms and 1 to 4 identical or different hetero atoms—in particular nitrogen, oxygen and/or sulphur—in the heteroaryl moiety and where appropriate 1 to 4 carbon atoms in the straight-chain or branched alkyl moiety and each of which is optionally monosubstituted or polysubstituted in the heteroaryl moiety by identical or different substituents from the series comprising halogen, alkyl, alkoxy, alkylthio, halogenoalkyl, halogenoalkoxy or halogenoalkylthio, each of which has 1 to 4 carbon atoms and if appropriate 1 to 9 identical $R^9$ represents in each case unsubstituted or substituted alkyl having 1 to 8 carbon atoms, unsubstituted or substituted alkenyl having 2 to 8 carbon atoms or unsubstituted or substituted alkinyl having 2 to 8 carbon atoms, suitable substituents in each case being: cyano, alkoxy having 1 to 4 carbon atoms or alkoxycarbonyl having 1 to 4 carbon atoms in the alkoxy moiety, furthermore $R^9$ represents aryl which has 6 to 10 carbon atoms which is unsubstituted or monosubstituted to polysubstituted by identical or different substituents, aralkyl which has 6 to 10 carbon atoms in the aryl moiety and 1 to 2 carbon atoms in the alkyl moiety and which is unsubstituted or monosubstituted to polysubstituted by identical or different substituents, suitable substituents which be mentioned being: halogen, alkyl having 1 to 4 carbon atoms, alkoxy having 1 to 4 carbon atoms, halogenoalkyl having 1 to 4 carbon atoms and 1 to 9 identical or different halogen atoms, or alkylidenedioxy having 1 to 2 carbon atoms, $R^9$ also represents heteroaryl having in each case 2 to 9 carbon atoms and 1 to 4 identical or different hetero atoms—in particular nitrogen, oxygen and/or sulphur—in the heteroaryl moiety, and R and Q independently of one another represent hydrogen, alkyl having 1 to 4 carbon atoms, alkoxy having 1 to 4 carbon atoms or halogenoalkyl having 1 to 4 carbon atoms and 1 to 9 identical or different halogen atoms.

Particularly preferred compounds of the formula (I) are those in which $R^1$ represents methyl, ethyl, n- or i-propyl or n-, i-, s- or t-butyl, or represents benzyl which is optionally monosubstituted to trisubstituted by identical or different substituents, suitable substituents being those mentioned in the case of $R^8$, $R^2$ represents dialkylamino having 1 to 4 carbon atoms in each of the individual straight-chain or branched alkyl moieties, or represents a radical $-Z-R^3$, where $R^3$ represents methyl, ethyl, n- or i-propyl or n-, i-, s- or t-butyl, or represents benzyl which is optionally monosubstituted to trisubstituted by identical or different substituents, suitable substituents being those mentioned in the case of $R^8$, and Z represents oxygen or sulphur;

A represents oxygen or sulphur, or represents one of the following groups $$-(CH_2)-_n, -CHR^4, -CR^4R^5 \text{ or } -NR^6,$$

where n represents the numbers 0, 1, 2 and 3, $R^4$ and $R^5$ in each case independently of one another represent straight-chain or branched alkyl having 1 to 4 carbon atoms; or together represent an alkyl chain having 2 to 5 carbon atoms, and $R^6$ represents straight-chain or branched alkyl having 1 to 4 carbon atoms, or represents a radical

where $R^7$ represents straight-chain or branched alkyl having 1 to 4 carbon atoms, straight-chain or branched alkoxy having 1 to 4 carbon atoms, or straight-chain or branched dialkylamino having 1 to 4 carbon atoms in each of the individual alkyl radicals, B represents the group CH—$R^8$ or NO—$R^9$, where $R^8$ represents phenyl, naphthyl, pyridinyl, pyrimidinyl, pyrazinyl, pyridazinyl, thienyl, furyl, pyrrolyl, thiazolyl, isothiazolyl, oxazolyl and isoxazolyl, in each case unsubstituted or in each case monosubstituted to trisubstituted by identical or different substituents, suitable substituents in each case being: fluorine, chlorine, bromine, cyano, nitro, methyl, ethyl, n- or i-propyl, n-, i-, s- or t-butyl, methoxy, ethoxy, n- or i-propoxy, methylenedioxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoximinoethyl, cyclopentyl, cyclohexyl, 1,3-propanediyl or 1,4-butanediyl, or phenyl, benzyl, phenoxy, benzyloxy, phenylthio or benzylthio, each of which is optionally monosubstituted to trisubstituted in the phenyl moiety by identical or different substituents from the series comprising fluorine, chlorine, bromine, methyl, ethyl, methoxy, ethoxy, methylthio, trifluoromethyl, difluoromethoxy, trifluoromethoxy and/or trifluoromethylthio;

$R^9$ represents in each case unsubstituted or substituted alkyl having 1 to 6 carbon atoms, unsubstituted or substituted alkenyl having 2 to 6 carbon atoms, and unsubstituted or substituted alkinyl having 2 to 6 carbon atoms, suitable substituents in each case being: cyano, methoxy, ethoxy, n- and i-propoxy, n-, i-, s- and t-butoxy, methoxycarbonyl, ethoxycarbonyl, n- and i-propoxycarbonyl, n-, i-, s- and t-butoxycarbonyl, $R^9$ furthermore represents phenyl or benzyl, in each case unsubstituted or monosubstituted to trisubstituted by identical or different substituents, substituents which may be mentioned being: fluorine, chlorine, bromine, methyl, ethyl, n- or i-propyl, n-, i-, s- or t-butyl, methoxy, ethoxy, n- or i-propoxy, n-, i-, s- or t-butoxy, halogenoalkyl having 1 or 2 carbon atoms and 1 to 5 identical or different fluorine or chlorine atoms, methylidenedioxy and ethylidenedioxy, and R and Q independently of one another represent hydrogen, methyl, ethyl, n- or i-propyl, methoxy, ethoxy or halogenoalkyl having 1 or 2 carbon atoms and 1 to 5 identical or different fluorine or chlorine atoms.

Especially preferred compounds of the formula (I) are those in which $R^1$ represents methyl, ethyl or benzyl, suitable benzyl substituents being those mentioned in the case of $R^8$, $R^2$ represents dimethylamino or diethylamino, or represents a radical —Z—$R^3$,
where
$R^3$ represents methyl, ethyl, n- or i-propyl or benzyl, and
Z represents oxygen or sulphur;
A represents oxygen or sulphur, or represents one of the following groups $-(CH_2)-_n$, $>CH-CH_3$, $>CH-C_2H_5$, $>CH-CH(CH_3)_2$, $>CH-C(CH_3)_3$, $>C(CH_3)_2$, $>C\!\!\bigcirc$ , $>N-COOCH_3$, $>N-COOC_2H_5$, $>N-\underset{\underset{O}{\|}}{C}-CH_3$ or $>N-\underset{\underset{O}{\|}}{C}-C_2H_5$, where
n represents the numbers 0, 1, 2 and 3,
B represents the group CH—$R^8$ or NO—$R^9$,
where
$R^8$ represents phenyl, naphthyl, pyridinyl, pyrimidinyl, pyrazinyl, pyridazinyl, thienyl, furyl, pyrrolyl, thiazolyl, isothiazolyl, oxazolyl or isoxazolyl, in each case unsubstituted or in each case monosubstituted to trisubstituted by identical or different substituents, suitable substituents in each case being: fluorine, chlorine, bromine, cyano, nitro, methyl, ethyl, n- or i-propyl, n-, i-, s- or t-butyl, methoxy, ethoxy, n- or i-propoxy, methylenedioxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoximinoethyl, cyclopentyl, cyclohexyl, 1,3-propanediyl, 1,4-butanediyl, or phenyl, phenoxy, benzyl, benzyloxy, phenylthio or benzylthio, each of which is optionally monosubstituted or disubstituted by identical or different substituents from the series comprising fluorine, chlorine, bromine, methyl and/or ethyl;
$R^9$ represents in each case unsubstituted or substituted alkyl having 1-6 carbon atoms, unsubstituted or substituted alkenyl having 2 to 4 carbon atoms and unsubstituted or substituted alkinyl having 2 to 4 carbon atoms, suitable substituents in each case being cyano, methoxycarbonyl, ethoxycarbonyl, methoxy or alkoxy;
$R^9$ furthermore represents phenyl or benzyl, in each case unsubstituted or monosubstituted or disubstituted by identical or different substituents, suitable substituents being: bromine, fluorine, chlorine, methoxy, ethoxy, methylenedioxy, methyl, ethyl and trifluoromethyl, and
R and Q independently of one another represent hydrogen or methyl.

Very especially preferred compounds of the formula (I) are those in which
$R^1$ represents methyl or ethyl,
$R^2$ represents methoxy, ethoxy, methylthio or dimethylamino,
A represents oxygen or sulphur, or represents one of the groups below $(CH_2)-_n$, $-\underset{|}{C}H-CH_3$ or $-\underset{|}{C}(CH_3)_2$ where
n represents the numbers 0, 1 or 2,
B represents the group CH—$R^8$ or NO—$R^9$,
where
$R^8$ represents phenyl, naphthyl, pyridinyl, pyrimidinyl, thienyl, furyl, thiazolyl, oxazolyl or isoxazolyl, each of which is unsubstituted, monosubstituted to trisubstituted by identical or different substituents, suitable substituents being: fluorine, chlorine, bromine, cyano, nitro, methyl, ethyl, methoxy, ethoxy, methylenedioxy, methylthio, trifluoromethyl, methoxycarbonyl, ethoxycarbonyl, cyclopentyl, cyclohexyl, phenoxy, phenylthio, benzyloxy or benzylthio;
$R^9$ represents methyl, ethyl, n- and i-propyl, n-, i- and t-butyl, n- and iso-amyl, allyl, methallyl, propargyl, benzyl, o-, m- and p-chlorobenzyl, o-, m- and p-methoxy-benzyl, o-, m- and p-methylbenzyl or o-, m- and p-fluorobenzyl, and
R and Q represent hydrogen.

The following substituted acrylic esters of the general formula (I)

$R\underset{B=CH-C=C-\underset{\underset{CH-R^2}{\|}}{C}-COOR^1}{\overset{A}{\diagup}\!\!\!\diagdown^Q}$ (I)

may be mentioned individually in addition to the compounds mentioned in the Preparation Examples:

TABLE 1

| $R^1$ | $R^2$ | A | R | Q | B |
|---|---|---|---|---|---|
| $CH_3$ | $OCH_3$ | — | H | H | CH-(2-Cl—$C_6H_4$) |
| $CH_3$ | $OCH_3$ | — | H | H | CH-(3-Cl—$C_6H_4$) |
| $CH_3$ | $OCH_3$ | — | H | H | CH-(2,3-$Cl_2$—$C_6H_3$) |
| $CH_3$ | $OCH_3$ | — | H | H | CH-(2,6-$Cl_2$—$C_6H_3$) |
| $CH_3$ | $OCH_3$ | — | H | H | CH-(2,5-$Cl_2$—$C_6H_3$) |
| $CH_3$ | $OCH_3$ | — | H | H | CH-(3,5-$Cl_2$—$C_6H_3$) |
| $CH_3$ | $OCH_3$ | — | H | H | CH-(2,4,6-$Cl_3$—$C_6H_4$) |
| $CH_3$ | $OCH_3$ | — | H | H | CH-(4-F—$C_6H_4$) |
| $CH_3$ | $OCH_3$ | — | H | H | CH-(4-$C_2H_5$—$C_6H_4$) |

TABLE 1-continued
| R¹ | R² | A | R | Q | B |
|---|---|---|---|---|---|
| CH₃ | OCH₃ | — | H | H | 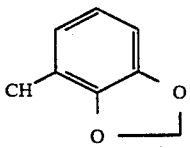 |
| CH₃ | OCH₃ | — | H | H | CH-(3,4-F₂—C₆H₃) |
| CH₃ | OCH₃ | — | H | H | 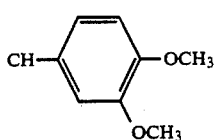 |
| CH₃ | OCH₃ | — | H | H | 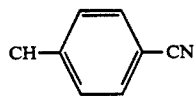 |
| CH₃ | OCH₃ | — | H | H | 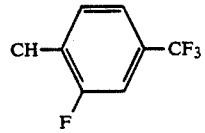 |
| CH₃ | OCH₃ | — | H | H | 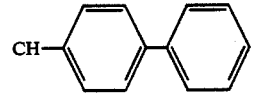 |
| CH₃ | OCH₃ | — | H | H | 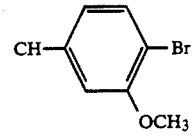 |
| CH₃ | OCH₃ | — | H | H | CH-(3-Cl-4-CF₃—C₆H₃) |
| CH₃ | OCH₃ | — | H | H | CH-(C₆Cl₅) |
| CH₃ | OCH₃ | — | H | H | 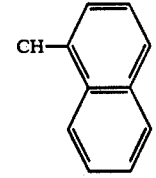 |
| CH₃ | OCH₃ | — | H | H | 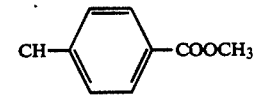 |
| CH₃ | OCH₃ | — | H | H | 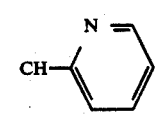 |
| CH₃ | OCH₃ | — | H | H | 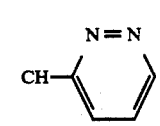 |

TABLE 1-continued

| R¹ | R² | A | R | Q | B |
|---|---|---|---|---|---|
| CH₃ | OCH₃ | — | H | H | CH-(pyrazinyl) |
| CH₃ | OCH₃ | — | H | H | CH-(pyrimidinyl) |
| CH₃ | OCH₃ | — | H | H | CH-(6-Cl-pyridin-3-yl) |
| CH₃ | OCH₃ | — | H | H | CH-(3-methylisoxazol-5-yl) |
| CH₃ | OCH₃ | — | H | H | CH-(3-ethylisoxazol-5-yl) |
| CH₃ | OCH₃ | — | H | H | CH-(thien-2-yl) |
| CH₃ | OCH₃ | — | H | H | CH-(fur-2-yl) |
| CH₃ | OCH₃ | — | H | H | CH-[2-(4-F—C₆H₄)-thiazol-5-yl] |
| CH₃ | OCH₃ | — | H | H | CH-(2-methylthiazol-5-yl) |
| CH₂CH₃ | OCH₃ | — | H | H | CH—C₂H₅ |
| CH₂CH₃ | OCH₃ | — | H | H | CH-(4-Cl—C₆H₄) |
| CH₂CH₃ | OCH₃ | — | H | H | CH-(3,4-Cl₂—C₆H₃) |
| CH₃ | OCH₂CH₃ | — | H | H | CH-[3,4-(CH₃)₂—C₆H₃] |
| CH₃ | OCH₂CH₃ | — | H | H | CH-(3,4-Cl₂—C₆H₃) |
| CH₃ | OCH₂CH₃ | — | H | H | CH-(4-Cl—C₆H₄) |
| CH₂CH₃ | OCH₂CH₃ | — | H | H | CH-(4-Br—C₆H₄) |
| CH₂CH₃ | OCH₂CH₃ | — | H | H | CH-(biphenyl-4-yl) |
| CH₂CH₃ | OCH₂CH₃ | — | H | H | CH-(naphth-2-yl) |
| CH₃ | OCH₃ | CH₂ | H | H | CH(2-Cl—C₆H₄) |
| CH₃ | OCH₃ | CH₂ | H | H | CH(3-Cl—C₆H₄) |
| CH₃ | OCH₃ | CH₂ | H | H | CH(3,4-F₂—C₆H₄) |
| CH₃ | OCH₃ | CH₂ | H | H | CH(2,3-Cl₂—C₆H₃) |

TABLE 1-continued

| R¹ | R² | A | R | Q | B |
|---|---|---|---|---|---|
| CH₃ | OCH₃ | CH₂ | H | H | 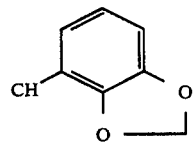 |
| CH₃ | OCH₃ | CH₂ | H | H | 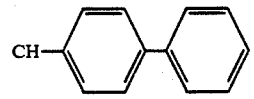 |
| CH₃ | OCH₃ | CH₂ | H | H | 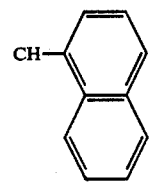 |
| CH₃ | OCH₃ | CH₂ | H | H | 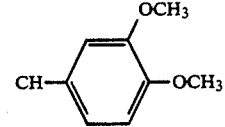 |
| CH₃ | OCH₃ | CH₂ | H | H | 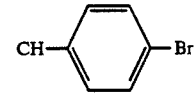 |
| CH₃ | OCH₃ | CH₂ | H | H | 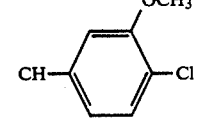 |
| CH₃ | OCH₃ | CH₂ | H | H | 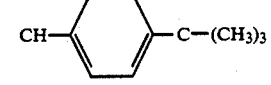 |
| CH₃ | SCH₃ | CH₂ | H | H | CHC₆H₅ |
| CH₃ | SCH₃ | CH₂ | H | H | CH(3,4-Cl₂—C₆H₃) |
| CH₃ | N(CH₃)₂ | CH₂ | H | H | CH(4-Br—C₆H₄) |
| CH₃ | N(CH₃)₂ | CH₂ | H | H | CHC₆H₅ |
| CH₃ | N(CH₃)₂ | CH₂ | H | H | CH(3,4-Cl₂—C₆H₃) |
| CH₃ | SCH₃ | CH₂ | H | H | CH(4-Br—C₆H₄) |
| CH₂C₆H₅ | OCH₃ | CH₂ | H | H | CHC₆H₅ |
| CH₂C₆H₅ | OCH₃ | CH₂ | H | H | CH(3,4-Cl₂—C₆H₃) |
| CH₂C₆H₅ | OCH₃ | CH₂ | H | H | CH(4-Br—C₆H₄) |
| CH₃ | OCH₃ | CH₂ | H | H | 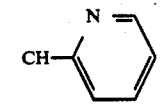 |
| CH₃ | OCH₃ | CH₂ | H | H | 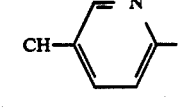 |
| CH₃ | OCH₃ | CH₂ | H | H | 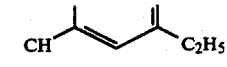 |

TABLE 1-continued

| R¹ | R² | A | R | Q | B |
|---|---|---|---|---|---|
| CH₃ | OCH₃ | CH₂ | | | CH=CH-C(CH₃)=N-O (isoxazole, 3-methyl-5-yl via CH) |
| CH₃ | OCH₃ | CH₂ | H | H | CH=C(S-C₆H₄-4-CH₃)-N= (thiazole with p-tolyl) |
| CH₃ | OCH₃ | CH₂ | H | H | CH=C(...)-N= bis-thiazole with N=C(CH₃)-S |
| CH₃ | OCH₃ | CH₂ | H | H | CH-(3-methylpyridazin-6-yl) (N=N) |
| CH₃ | OCH₃ | CH₂ | H | H | CH-(thiophen-2-yl) |
| CH₃ | OCH₃ | CH₂ | H | H | CH-(furan-2-yl) |
| CH₃ | OCH₂H₃ | CH₂ | H | H | CH-(6-methoxypyridin-3-yl) |
| CH₃ | OCH₂CH₃ | CH₂ | H | H | CH-(pyridin-4-yl) |
| CH₂CH₃ | OCH₃ | CH₂ | H | H | CH-(pyridin-3-yl) |
| CHCH₃ | OCH₃ | CH₂ | H | H | CH—C₆H₅ |
| CH₃ | OCH₃ | CH₂ | H | H | CH-(2,6-F₂—C₆H₃) |
| CH₃ | OCH₃ | CH₂ | H | H | CH-(2-Cl-6-F—C₆H₃) |
| CH₃ | OCH₃ | CH₂ | H | H | CH-(3-COOCH₃—C₆H₄) |
| CH₂CH₃ | OCH₃ | CH₂ | H | H | CH-(3-CF₃—C₆H₄) |
| CH₃ | OCH₃ | CH₂ | H | H | CH-(4-SCF₃—C₆H₄) |
| CH₃ | OCH₃ | CH₂ | H | H | CH-(4-OCF₃—C₆H₄) |
| CH₃ | OCH₃ | CH₂ | H | H | CH-(4-CN—C₆H₄) |

TABLE 1-continued

| R¹ | R² | A | R | Q | B |
|---|---|---|---|---|---|
| CH₃ | OCH₃ | CH₂CH₂ | H | H | CH(2-Cl—C₆H₄) |
| CH₃ | OCH₃ | CH₂CH₂ | H | H | CH(3-Cl—C₆H₄) |
| CH₃ | OCH₃ | CH₂CH₂ | H | H | CH(2,3-Cl₂—C₆H₃) |
| CH₃ | OCH₃ | CH₂CH₂ | H | H | CH(4-Br—C₆H₄) |
| CH₃ | OCH₃ | CH₂CH₂ | H | H | CH(3-CF₃—C₆H₄) |
| CH₃ | OCH₃ | CH₂CH₂ | H | H | CH(3-OCH₃-4-Cl—C₆H₃) |
| CH₃ | OCH₃ | CH₂CH₂ | H | H | CH(3-OCH₃—C₆H₄) |
| CH₃ | OCH₃ | CH₂CH₂ | H | H | CH(3-CH₃—C₆H₄) |
| CH₃ | OCH₃ | CH₂CH₂ | H | H | CH(4-F—C₆H₄) |
| CH₃ | OCH₃ | CH₂CH₂ | H | H | CH-(methylenedioxyphenyl) |
| CH₃ | OCH₃ | CH₂CH₂ | H | H | CH-(3-Cl-4-OCH₃-phenyl) |
| CH₃ | OCH₃ | CH₂CH₂ | H | H | CH-(3,4-diOCH₃-phenyl) |
| CH₃ | OCH₃ | CH₂CH₂ | H | H | CH-(4-biphenyl) |
| CH₃ | OCH₃ | CH₂CH₂ | H | H | CH-(4-(phenylethynyl)phenyl) |
| CH₃ | OCH₃ | CH₂CH₂ | H | H | CH-(4-phenoxyphenyl) |
| CH₃ | OCH₃ | CH₂CH₂ | H | H | CH-(4-(4-cyanophenoxy)phenyl) |
| CH₃ | OCH₃ | CH₂CH₂ | H | H | CH-(4-methylphenyl) |
| CH₃ | OCH₃ | CH₂CH₂ | H | H | CH-(4'-fluoro-4-biphenyl) |
| CH₃ | OCH₃ | CH₂CH₂ | H | H | CH-(2-F-3-Cl—C₆H₃) |
| CH₃ | OCH₃ | CH₂CH₂ | H | H | CH-(2-Cl-3-F—C₆H₃) |
| CH₃ | OCH₃ | CH₂CH₂ | H | H | CH-(3-phenoxyphenyl) |

TABLE 1-continued
| R¹ | R² | A | R | Q | B |
|---|---|---|---|---|---|
| CH₃ | OCH₃ | CH₂CH₂ | H | H | 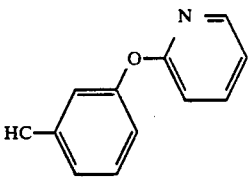 |
| CH₃ | OCH₃ | CH₂CH₂ | H | H | 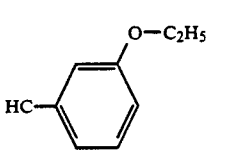 |
| CH₃ | OCH₃ | CH₂CH₂ | H | H | 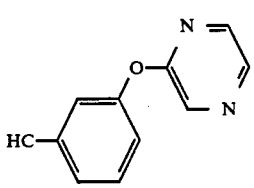 |
| CH₃ | OCH₃ | CH₂CH₂ | H | H | 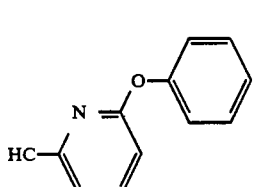 |
| CH₃ | OCH₃ | CH₂CH₂ | H | H | CH-[2,4,6-(CH₃)₃C₆H₂] |
| CH₃ | OCH₃ | CH₂CH₂ | H | H | 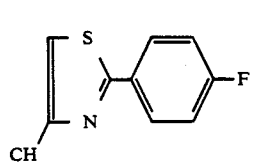 |
| CH₂CH₃ | OCH₃ | CH₂CH₂ | H | H | CH—C₆H₅ |
| CH₂CH₃ | OCH₃ | CH₂CH₂ | H | H | CH-(2,4-Cl₂—C₆H₃) |
| CH₂CH₃ | OCH₃ | CH₂CH₂ | H | H | CH-(3,4-Cl₂—C₆H₃) |
| CH₃ | OCH₃ | — | H | H | 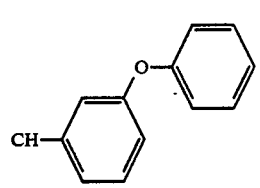 |
| CH₃ | OCH₃ | — | H | H | 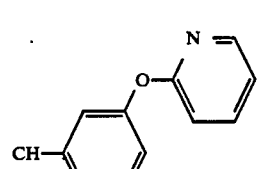 |
| CH₃ | OCH₃ | — | H | H | 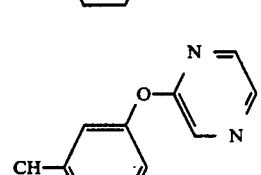 |

TABLE 1-continued

| R¹ | R² | A | R | Q | B |
|---|---|---|---|---|---|
| CH₃ | OCH₃ | — | H | H | CH-pyridine-O-phenyl |
| CH₃ | OCH₃ | — | H | H | CH-phenyl-O-phenyl |
| CH₃ | OCH₃ | CH₂ | H | H | HC-phenyl-O-phenyl |
| CH₃ | OCH₃ | CH₂ | H | H | HC-phenyl-O-pyrazine |
| CH₃ | OCH₃ | CH₂ | H | H | HC-phenyl-O-pyrimidine |
| CH₃ | OCH₃ | CH₂ | H | H | HC-phenyl-O-(4-CH₃-phenyl) |
| CH₃ | OCH₃ | CH₂ | H | H | HC-phenyl-O-(4-C₂H₅-phenyl) |
| CH₃ | OCH₃ | O | H | H | HC-phenyl-O-phenyl |
| CH₃ | OCH₃ | O | H | H | HC-phenyl-O-pyridine |

TABLE 1-continued

| R¹ | R² | A | R | Q | B |
|---|---|---|---|---|---|
| CH₃ | OCH₃ | O | H | H | 3-(pyrimidin-2-yloxy)phenyl |
| CH₃ | OCH₃ | O | H | H | 3-(pyrazin-2-yloxy)phenyl |
| CH₃ | OCH₃ | O | H | H | 4-(4-chlorophenoxy)phenyl |
| CH₃ | OCH₃ | S | H | H | 3-phenoxyphenyl |
| CH₃ | OCH₃ | S | H | H | 4-phenoxyphenyl |
| CH₃ | OCH₃ | S | H | H | 3-(3-methylphenoxy)phenyl |
| CH₃ | OCH₃ | S | H | H | 4-(phenoxy)pyridin-2-yl |
| CH₃ | OCH₃ | S | H | H | 4-(phenylthio)pyridin-2-yl |
| CH₃ | OCH₃ | C(CH₃)₂ | H | H | 3-(4-trifluoromethylphenylthio)phenyl |

TABLE 1-continued
| R¹ | R² | A | R | Q | B |
|---|---|---|---|---|---|
| CH₃ | OCH₃ | C(CH₃)₂ | H | H | 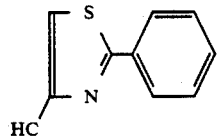 |
| CH₃ | OCH₃ | C(CH₃)₂ | H | H | 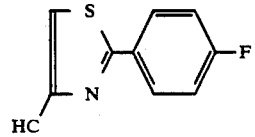 |
| CH₃ | OCH₃ | C(CH₃)₂ | H | H | 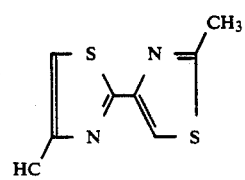 |
| CH₃ | OCH₃ | C(CH₃)₂ | H | H | 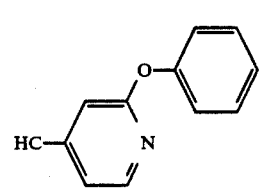 |
| CH₃ | OCH₃ | NCH₃ | H | H | 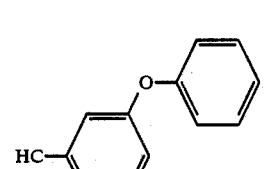 |
| CH₃ | OCH₃ | NCOCH₃ | H | H | 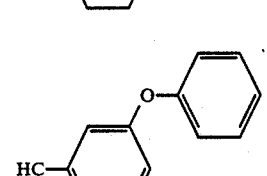 |
| CH₃ | OCH₃ | NCOOC₂H₅ | H | H | 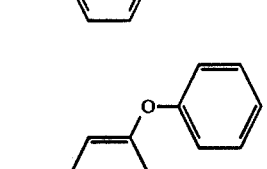 |
| CH₃ | OCH₃ | 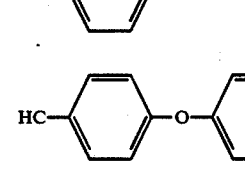 | H | H | 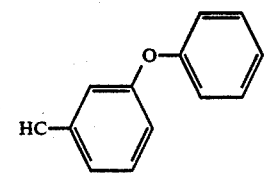 |
| CH₃ | OCH₃ | O | H | H | CH-(2,3-Cl₂—C₆H₃) |

TABLE 1-continued

| R¹ | R² | A | R | Q | B |
|---|---|---|---|---|---|
| CH₃ | OCH₃ | O | H | H | 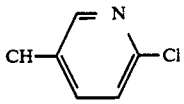 |
| CH₃ | OCH₃ | O | H | H | 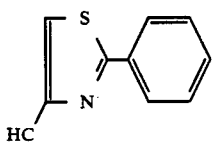 |
| CH₃ | OCH₃ | O | H | H | CH-(3-F-4-Cl—C₆H₃) |
| CH₃ | OCH₃ | S | H | H | CH-(2,6-Cl₂—C₆H₃) |
| CH₃ | OCH₃ | S | H | H | CH-(2,4,6-Cl₃—C₆H₂) |
| CH₃ | OCH₃ | S | H | H | 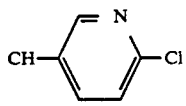 |
| CH₃ | OCH₃ | S | H | H | 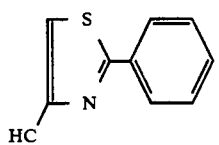 |
| CH₃ | OCH₃ | N—COOC₂H₅ | H | H | CH—C₆H₅ |
| CH₃ | OCH₃ | N—COOC₂H₅ | H | H | 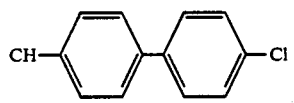 |
| CH₃ | OCH₃ | N—COOC₂H₅ | H | H | 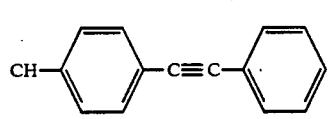 |
| CH₃ | OCH₃ | N—COOC₂H₅ | H | H | 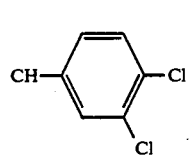 |
| CH₃ | OCH₃ | N—CH₃ | H | H | CH-(2-F—C₆H₄) |
| CH₃ | OCH₃ | N—CH₃ | H | H | CH-(3-F—C₆H₄) |
| CH₃ | OCH₃ | N—CO—CH₃ | H | H | CH—C₆H₅ |
| CH₃ | OCH₃ | N—CO—CH₃ | H | H | 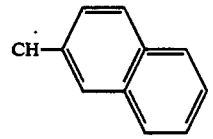 |
| CH₃ | OCH₃ | ⬡ | H | H | CH—C₆H₅ |
| CH₃ | OCH₃ | ⬡ | H | H | CH-(3,4-Cl₂—C₆H₃) |

TABLE 1-continued

| R¹ | R² | A | R | Q | B |
|---|---|---|---|---|---|
| CH₃ | OCH₃ |  | H | H | CH-(4-Cl—C₆H₄) |
| CH₂CH₃ | OCH₃ |  | H | H | CH—C₆H₅ |
| CH₃ | OCH₃ | — | H | H | N—OCH₃ |
| CH₃ | OCH₃ | — | H | H | N—OCH₂—CH=CH₂ |
| CH₃ | OCH₃ | — | H | H | N—OCH₂—C≡CH |
| CH₃ | OCH₃ | — | H | H | N—OCH₂—C₆H₅ |
| CH₃ | OCH₃ | — | H | H | N—O—C₆H₅ |
| CH₃ | OCH₃ | — | H | H | N—OCH₂—CH₂—CH₂CH₃ |
| CH₃ | OCH₃ | — | H | H | N—OCH₂—C≡N |
| CH₂CH₃ | OCH₃ | CH₂ | H | H | N—OCH₃ |
| CH₂CH₃ | OCH₃ | CH₂ | H | H | N—OCH₂—CH=CH₂ |
| CH₃ | OCH₃ | CH₂ | H | H | N—OCH₂-(4-Cl—C₆H₄) |
| CH₃ | OCH₃ | CH₂ | H | H | N—OCH₂COOCH₃ |
| CH₃ | OCH₃ | CH₂ | H | H | N—OCH₂COOC₂H₅ |
| CH₃ | OCH₃ | CH₂ | H | H | N—OCH₂—C≡CH |
| CH₃ | OCH₃ | CH₂ | H | H | N—OCH₂—C≡N |
| CH₃ | OCH₃ | CH₂CH₂ | H | H | NOCH₃ |
| CH₃ | OCH₃ | CH₂CH₂ | H | H | NOC₂H₅ |
| CH₃ | OCH₃ | CH₂CH₂ | H | H | NO—CH₂—CH=CH₂ |
| CH₃ | OCH₃ | O | H | H | NO—CH₂—CH=CH₂ |
| CH₃ | OCH₃ | O | H | H | NO—CH₃ |
| CH₃ | OCH₃ | O | H | H | NO—CH₂COOCH₃ |
| CH₃ | OCH₃ | S | H | H | NOCH₃ |
| CH₃ | OCH₃ | S | H | H | NOCH₂CH=CH₂ |
| CH₃ | OCH₃ | S | H | H | NOCH₂C≡CH |
| CH₃ | OCH₃ | NCH₃ | H | H | NOCH₃ |
| CH₃ | OCH₃ | NCH₃ | H | H | NOCH₂CH=CH₂ |
| CH₃ | OCH₃ | N—C(=O)—CH₃ | H | H | NOCH₃ |
| CH₃ | OCH₃ | N—C(=O)—CH₃ | H | H | NOCH₂CH=CH₂ |
| CH₃ | OCH₃ | N—COOCH₃ | H | H | NOCH₃ |
| CH₃ | OCH₃ | N—COOC₂H₅ | H | H | NOCH₂CH=CH₂ |
| CH₃ | OCH₃ | C(CH₃)₂ | H | H | NOC₂H₅ |
| CH₃ | OCH₃ | C(CH₃)₂ | H | H | NOCH₂CH=CH₂ |
| CH₃ | OCH₃ | CH—C(CH₃)₃ | H | H | NO—C₃H₇-n |
| CH₃ | OCH₃ | CH—C(CH₃)₃ | H | H | NOCH₂CH=CH₂ |
| CH₃ | OCH₃ |  | H | H | CN—C₃H₇-n |
| CH₃ | OCH₃ |  | H | H | NO—C₃H₇ |
| CH₃ | OCH₃ |  | H | H | NOCH₂CH=CH₂ |
| CH₃ | OCH₃ |  | H | H | NOCH₂CH=CH₂ |
| CH₃ | OCH₃ | CH—CH₃ | H | H | NOCH₂CH=CH₂ |
| CH₃ | OCH₃ | CH—CH₃ | H | H | NOCH₂C≡CH |

TABLE 1-continued

| R¹ | R² | A | R | Q | B |
|---|---|---|---|---|---|
| CH₃ | OCH₃ | 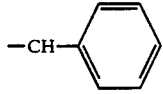 | H | H | NOCH₂CH₃ |

If, for example, methyl 3-hydroxy-2-[2-(2-(2,3-difluorophenyl)-ethenyl)-cyclopenten-1-yl]-acrylate and dimethyl sulphate are used as the starting substances, the course of the reaction of process (a) according to the invention may be represented by the following equation:

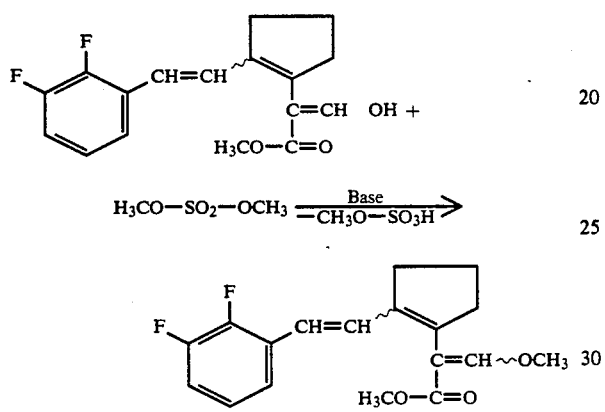

If, for example, methyl 2-[[2-(4-chloro-3-methoxyphenyl)-ethenyl]-cyclohexen-1-yl]-acetate and dimethylformamide dimethyl acetal are used as the starting substances, the course of the reaction of process (b) according to the invention may represented by the following equation:

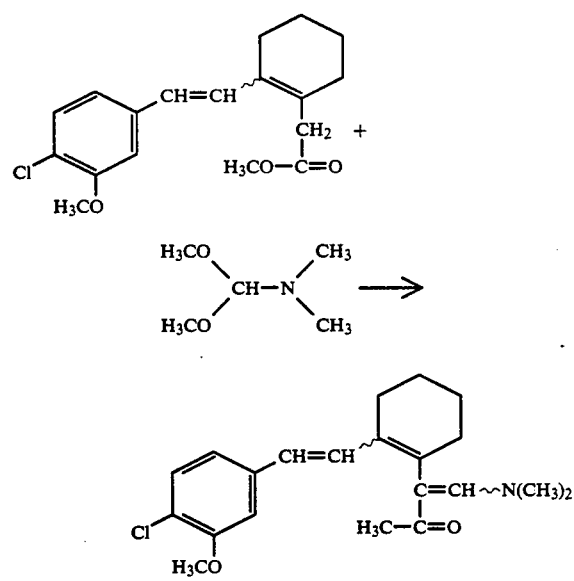

If, for example, methyl 2-oxo[[2-(2-phenyl)ethenyl]-cyclohepten-1-yl]-acetate and [(methylthio)(trimethylsilyl)]-methylenelithium are used as the starting compounds, the course of the reaction of process (c) according to the invention may be represented by the following equation:

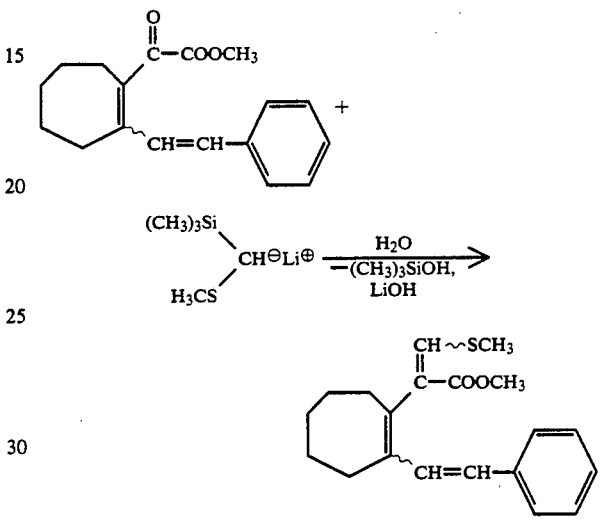

If, for example, methyl 3-methanesulphonyloxy[[2-(pyridin-2-yl)-ethenyl]-4-thia-cyclohexen-1-yl]acrylate and methyl mercaptan are used as the starting substances, the course of the reaction of process (d) according to the invention may be represented by the following equation:

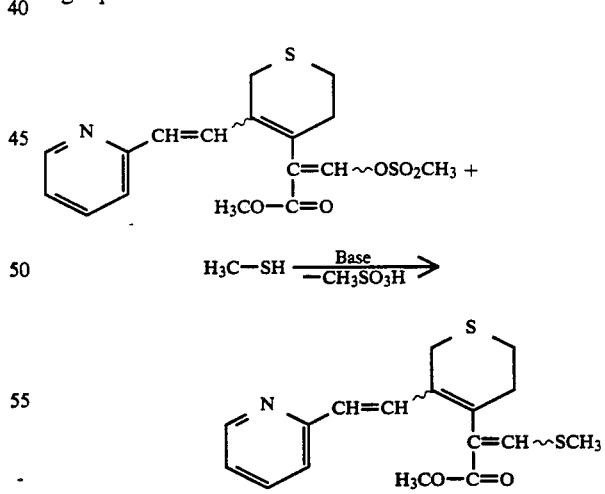

Formula (II) provides a general definition of the hydroxyacrylic esters or their alkali metal salts required as starting substances for carrying out process (a) according to the invention. In this formula (II), R¹, A, B, R and Q preferably represent those radicals which have already been mentioned in connection with the description of the substances of formula (I) according to the invention as being preferred for these substituents.

M preferably represents hydrogen, or represents a lithium, sodium or potassium cation.

The hydroxyacrylic esters of the formula (II) which are required for carrying out process (a) according to the invention were hitherto unknown and are a subject of the invention.

They are obtained when substituted acetic esters of the formula (IV)

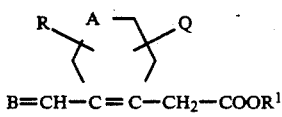

B=CH—C=C—CH$_2$—COOR$^1$    (IV)

in which
R$^1$, A, B, R and Q have the abovementioned meanings, are reacted with formic esters of the formula (X)

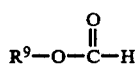    (X)

in which
R$^9$ represents alkyl, in particular methyl or ethyl, if appropriate in the presence of a diluent, such as, for example, dimethylformamide, and if appropriate in the presence of a basic reaction auxiliary, such as, for example, sodium hydride, at temperatures of from −20° C. to +50° C.

Formic esters of the formula (X) are generally known compounds of organic chemistry.

Formula (III) provides a general definition of the alkylating agents furthermore required as starting substances for carrying out process (a) according to the invention. In this formula (III), R$^3$ preferably represents those radicals which have already been mentioned in connection with the description of the substances of the formula (I) according to the invention as being preferred for this substituent.

E$^1$ represents a leaving group customary in the case of alkylating agents, preferably an optionally substituted alkyl, alkoxy or arylsulphonyloxy radical, such as, for example, a methoxysulphonyloxy radical, an ethoxysulphonyloxy radical or a p-toluenesulphonyloxy radical, or represents halogen, in particular chlorine, bromine or iodine.

The alkylating agents of the formula (III) are generally known compounds of organic chemistry.

The substituted acetic ester of the general formula (IV), which are required as starting substances for carrying out process (b) according to the invention and for the synthesis of the precursors of the formula (II), are new and a subject of the invention. In this formula (IV), R$^1$, A and B preferably represent those radicals which have already been mentioned in connection with the description of the substances of the formula (I) according to the invention as being preferred for these substituents.

The compounds of the formula (IV) are obtained:
a) in the event that R$^1$, A, R and Q have the abovementioned meaning and B represents the group N—O—R$^9$,
where
R$^9$ has the abovementioned meaning,
by reacting aldehydes of the general formula (XI)

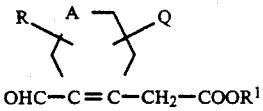

OHC—C=C—CH$_2$—COOR$^1$    (XI)

in which
R$^1$, A, R and Q have the abovementioned meanings, with compounds of the general formula (XII)

R$^9$—O—NH$_2$    (XII)

in which
R$^9$ has the abovementioned meaning,
if appropriate in the presence of a diluent, such as, for example, methanol, at temperatures of from −20° C. to +50° C. (cf. Preparation Examples).

Compounds of the general formula (XII) are generally known compounds of organic chemistry, or they can be obtained in analogy to generally known processes (cf., for example, GB 1,042,191; Tetrahedron Lett. 23 2955-6 (1982); DE- OS (German Published Specification) 3,615,473).

They are also obtained:
b) in the event that R$^1$, A, R and Q have the abovementioned meaning and B represents the group CH—R$^8$,
where
R$^8$ has the abovementioned meaning, by reacting, aldehydres of the general formula (XI)

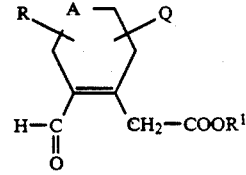    (XI)

in which
R$^1$, A, R and Q have the abovementioned meanings,
α) with phosphonium compounds of the general formula (XIII)

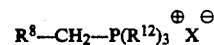    (XIII)

R$^8$—CH$_2$—P(R$^{12}$)$_3$ $^\oplus$ X $^\ominus$ in which
R$^8$ has the abovementioned meaning,
R$^{12}$ represents aryl which is optionally substituted by methyl, ethyl, methoxy or ethoxy, preferably phenyl, and
X represents halogen, preferably bromine or chlorine; or
β) with reagents of the general formula (XIV)

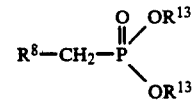    (XIV)

in which
R$^8$ has the abovementioned meaning and $R^{13}$ represents $C_{1-4}$-alkyl, particularly preferably methyl, ethyl or n-butyl, using a solvent which is inert under the reaction conditions, such as, for example, tetrahydrofuran, and if appropriate a basic auxiliary, such as, for example, sodium hydride, butyllithium or potassium tert.-butylate, at temperatures of from $-80°$ C. to $+60°$ C., in the sense of a WITTIG reaction or of a HORNER-WITTIG reaction (cf. Preparation Examples).

Both the compounds of the general formula (XIII) and those of the general formula (XIV) are generally known compounds of organic chemistry, or they can synthesized in analogy to generally known processes (cf. for example, L.-F. Tietze, Th. Eicher "Reaktionen und Synthesen im organisch-chemischen Praktikum [Reactions and Syntheses in the Laboratory Practical in Organic Chemistry]", p. 165 and 167, Thieme Verlag Stuttgart, New York 1981).

The aldehydes of the general formula (XI) are known in some cases and/or can be synthesized in analogy to known processes (cf., inter alia, J. Chem. Soc. Perkin I 2005 (1974)).

Formulae (Va) and (Vb) provide general definitions of the formamides and their derivatives furthermore required as starting substances for carrying out process (b) according to the invention. In these formulae (Va) and (Vb), $R^{2-1}$ preferably represents dialkylamino having 1 to 6, in particular 1 to 4, carbon atoms in each of the individual straight-chain or branched alkyl moieties. $R^{2-1}$ especially preferably represents dimethylamino or diethylamino.

$R^{10}$ and $R^{11}$ are preferably independent of one another and represent in each case straight-chain or branched alkoxy having 1 to 4 carbon atoms, in particular methoxy or ethoxy, or represent a dialkylamino radical having 1 to 6, in particular 1 to 4, carbon atoms in each of the individual straight-chain or branched alkyl moieties.

The formamides of the formula (Va) and their derivatives of the formula (Vb) are generally known compounds of organic chemistry.

Formula (VI) provides a general definition of the ketocarboxylic acid derivatives required as starting substances for carrying out process (c) according to the invention.

In this formula (VI), $R^1$, A, B, R and Q preferably represent those radicals which have already been mentioned in connection with the description of the substances of the formula (I) according to the invention as being preferred for these substituents.

The ketocarboxylic acid derivatives of the general formula (VI) are known in some cases, and/or they can be prepared by generally known processes, such as, for example, by oxidizing compounds of the general formula (IV) with the aid of a suitable oxidant, such as, for example, pyridinium chlorochromate or pyridinium dichromate, and using suitable inert diluents, for example chlorinated hydrocarbons, such as dichloromethane, at temperatures of from $+20°$ C. to $+100°$ C. Pyridinium chlorochromate and pyridinium dichromate are generally known compounds of organic chemistry.

Formula (VII) provides a general definition of the organometallic compounds furthermore required as starting substances for carrying out process (c) according to the invention. In this formula (VII), $R^3$ preferably represents those radicals which have already been mentioned in connection with the description of the substances of the formula (I) according to the invention as being preferred for this substituent.

The organometallic compounds of the formula (VII) are known (cf., for example, J. Org. Chem. 33, 780 [1968]; Org Chem. 37, 939 [1972]).

Formula (VIII) provides a general definition of the substituted acrylic esters required as starting substances for carrying out process (d) according to the invention. In this formula (VIII), $R^1$, A, B, R and Q preferably represent those radicals which have already been mentioned in connection with the description of the substances of the formula (I) according to the invention as being preferred for these substituents.

$E^2$ preferably represents a suitable acyloxy or sulphonyloxy radical, in particular an acetoxy, a methanesulphonyloxy or a p-toluenesulphonyloxy radical.

The substituted acrylic esters of the formula (VIII) were hitherto unknown.

They are obtained when hydroxyacrylic esters of the formula (II)

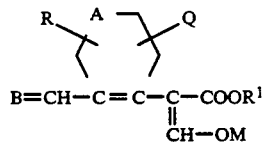

in which

M, $R^1$, A, B, R and Q have the abovementioned meanings, are reacted with acid chlorides of the formula (XIV)

$R^{14}$—Cl (XIV)

in which $R^{14}$ represents an acyl or sulphonyl radical, in particular an acetyl radical, a methanesulphonyl radical or a p-toluenesulphonyl radical, if appropriate in the presence of a diluent, such as, for example, dichloromethane, and if appropriate in the presence of an acid-binding agent such as, for example, triethylamine or pyridine, at temperatures of from $-20°$ C. to $+120°$ C.

Acid chlorides of the formula (XIV) are generally known compounds of organic chemistry.

Formula (IX) provides a general definition of the thiols furthermore required as starting substances for carrying out process (d) according to the invention. In this formula (IX), $R^3$ preferably represents those radicals which have already been mentioned in connection with the description of the substances of the formula (I) according to the invention as being preferred for this substituent.

The thiols of the formula (IX) are generally known compounds of organic chemistry.

Suitable diluents for carrying out process (a) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, or sulphoxides, such as dimethyl sulphoxide.

If appropriate, process (a) according to the invention can also be carried out in a two-phase system, such as, for example, water/toluene or water/dichloromethane, if appropriate in the presence of a phase transfer catalyst. Examples of such catalysts which may be mentioned are: tetrabutylammonium iodide, tetrabutylammonium bromide, tributyl-methylphosphonium bromide, trimethyl-$C_{13}/C_{15}$-alkylammonium chloride, dibenzyl-dimethyl-ammonium methylsulphate, dimethyl-$C_{12}/C_{14}$-alkylbenzylammonium chloride, tetrabutylammonium hydroxide, 15-crown-5, 18-crown-6, triethylbenzylammonium chloride, trimethylbenzylammonium chloride or tris-[2-(2-methoxyethoxy)-ethyl]-amine.

Process (a) according to the invention is preferably carried out in the presence of a suitable basic reaction auxiliary. Suitable basic reaction auxiliaries are all inorganic and organic bases which can customarily be used. The following are preferably used: hydrides, hydroxides, amides, alcoholates, carbonates or hydrogen carbonates of alkali metals, such as, for example, sodium hydride, sodium amide, sodium hydroxide, sodium methylate, sodium ethylate, potassium t-butylate, sodium carbonate or sodium hydrogen carbonate, and also tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU).

When carrying out process (a) according to the invention, the reaction temperatures can be varied within a substantial range. In general, the process is carried out at temperatures of from $-30°$ C. to $+120°$ C., preferably at temperatures of from $-20°$ C. to $+60°$ C.

For carrying out process (a) according to the invention, 1.0 to 10.0 moles, preferably 1.0 to 5.0 moles, of alkylating agent of the formula (III) and, if appropriate, 1.0 to 5.0 moles, preferably 1.0 to 2.0 moles, of reaction auxiliary are generally employed per mole of 3-hydroxyacrylic ester or of a corresponding alkali metal salt of the formula (II). In this context, it is also possible to prepare the 3-hydroxyacrylic esters or their alkali metal salts of the formula (II) which are required as starting compounds for carrying out process (a) according to the invention, in a preceding reaction directly in the reaction vessel, and to react them further directly from the reaction mixture with the alkylating agent of the formula (III) according to process (a) according to the invention, without isolation ("one-pot process"). The reaction is carried out and the reaction products are worked up and isolated by generally customary methods (cf. also the Preparation Examples).

Suitable diluents for carrying out process (b) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, or ethers, such as diethyl ether, dioxane, tetrahydrofuran or ethylene glycol dimethyl ether or ethylene glycol diethyl ether.

However, it is also possible to carry out process (b) according to the invention without adding a diluent.

When carrying out process (b) according to the invention, the reaction temperatures can be varied within a substantial range. In general, the process is carried out at temperatures of from $-20°$ C. to $+200°$ C., preferably at temperatures of from $0°$ C. to $150°$ C.

For carrying out process (b) according to the invention, 1.0 to 30.0 moles, preferably 1.0 to 15.0 moles, of formamide of the formula (Va) or of a corresponding derivative of the formula (Vb) are generally employed per mole of substituted acetic ester of the formula (IV).

The reaction is carried out and the reaction products are worked up and isolated by generally customary methods (cf. in this context also G. Mathieu; J. Weill-Raynal "Formation of C-C-Bonds", Vol. I; p. 229-244; Thieme Verlag Stuttgart 1973).

Suitable diluents for carrying out process (c) according to the invention are inert organic solvents. These include, in particular, aliphatic, alicyclic or aromatic hydrocarbons, such as, for example, benzene, toluene, xylene, petroleum ether, hexane or cyclohexane, or ethers, such as diethyl ether, dioxane, tetrahydrofuran or ethylene glycol dimethyl ether or ethylene glycol diethyl ether.

When carrying out process (c) according to the invention, the reaction temperatures can be varied within a substantial range. In general, the process is carried out at temperatures of from $-100°$ C. to $+100°$ C., preferably at temperatures of from $-80°$ C. to $+50°$ C.

For carrying out process (c) according to the invention, 1.0 to 1.5 moles, preferably 1.0 to 1.2 moles, of an organometallic compound of the formula (VII) are generally employed per mole of ketocarboxylic acid derivative of the formula (VI). The reaction is carried out and the reaction products are worked up and isolated by known processes (cf., for example, J. Org. Chem. 33, 780 [1968]; J. Org. Chem. 37, 939 [1972]).

Suitable diluents for carrying out process (d) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

Process (b) according to the invention is preferably carried out in the presence of a suitable reaction auxiliary. Suitable as reaction auxiliaries are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, or tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out process (d) according to the invention, the reaction temperatures can be varied within a substantial range. In general, the process is carried out at temperatures of from $-20°$ C. to $180°$ C., preferably at temperatures of from $0°$ C. to $150°$ C.

Depending on the boiling point of the reactants used, the process according to the invention may also be carried out under pressure, for example when lower-boiling thiols of the formula (IX) are employed.

In this case, it is preferred to carry out the process at the pressure which is established under the reaction conditions when the reactants are heated to the reaction temperature required.

For carrying out process (d) according to the invention, 1.0 to 20.0 moles, preferably 1.0 to 5.0 moles, of thiol of the formula (IX) and if appropriate 1.0 to 5.0 moles, preferably 1.0 to 1.5 moles, of reaction auxiliary are generally employed per mole of substituted acrylic ester of the formula (VIII). The reaction is carried out and the reaction products are worked up and isolated by generally customary methods.

The active compounds according to the invention have a powerful action against pests and can be employed in practice for combating undesired harmful organisms. The active compounds are suitable for use as plant protection agents, in particular as fungicides and insecticides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Ptthium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success for protectively combating Venturia species on apples, or for protectively combating rice diseases, such as, for example, against the causative organism of rice blast disease (*Pyricularia oryzae*) or protectively combating Erysiphe species on barley or wheat, or for protectively combating on *Leptosphaeria nodorum* species on wheat, or for protectively combating *Cochliobolus sativus* species and pyrenophora species on barley.

Moreover, the active compounds according to the invention also show fungicidal action against Plasmopara, Cercosporella and Sclerotinia, and also a good in-vitro activity.

To a certain extent, the new intermediates of the formula (IV) also show a fungicidal action.

In addition, the active compounds are suitable for combating animal pests, preferably arthropods and nematodes, in particular insects and arachnida encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quad-* rata, Cimex lectularius, Rhodnius prolixus and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp., Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Globedera ssp., Meloidogyne spp., Aphelenchoides spp., Longidorus spp., Xiphinema spp. and Trichodorus spp.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents and/or foam-forming agents. In the case of the use of water as an extender, organic solvents can, for example, also used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides and in mixtures with fertilizers and growth regulators.

The active compounds can be used as such, in the form of their formulations, or the use forms prepared from these formulations, such as ready-to-use solutions, suspensions, wettable powders, pastes, soluble powders, dusts and granules. They are applied in a customary manner, for example by watering, spraying, atomizing, scattering, dusting, foaming, brushing on and the like. It is furthermore possible to apply the active compounds using the ultra-low-volume method, or to inject the preparation of active compound, or the active compound itself, into the soil. It is also possible to treat the seeds of the plants.

In the treatment of parts of plants, the concentrations of active compound can be varied in the use forms in a substantial range. They are generally between 1 and 0.0001% by weight, preferably between 0.5 and 0.001%.

In the treatment of seeds, amounts of active compound of from 0.001 to 50 g per kilogram of seed, preferably 0.01 to 10 g, are generally required.

In the treatment of the soil, concentrations of active compound of from 0.00001 to 0.1% by weight, preferably of from 0.0001 to 0.02%, are required at the site of action.

PREPARATION EXAMPLES

Example 1

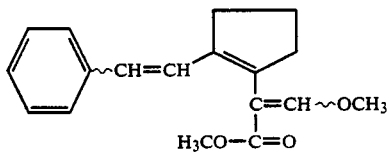

A solution of 5.00 g (20.63 mmol) of methyl 1-(2-phenyl-ethenyl)-2-cyclopenteneacetate in 30 ml of methyl formate is added dropwise at 0°–10° C. to a stirred suspension of 1.24 g (41.26 mmol) of sodium hydride (80% strength suspension) in 30 ml of dimethylformamide. The suspension, which is initially crimson red, dissolves as the reaction proceeds further. After the mixture has been stirred for about 4 hours, the formation of the enol is complete. 5.20 g (41.23 mmol) of dimethyl sulphate are now added dropwise at about 20° C. with stirring, and stirring is continued until the reaction is complete.

For working up, the mixture is stirred with an excess of saturated sodium hydrogen carbonate solution and extracted with ethyl acetate, the combined extracts are dried over anhydrous magnesium sulphate, filtered and concentrated, and the residue which remains is purified by column chromatography on silica gel (eluent: dichloromethane/n-hexane 1:1). This gives 2.00 g (34.1% of theory) of methyl E-3-methoxy-2-[2-(2-phenylethenyl)cyclopenten-1-yl]acrylate of m.p. 107° C. and a cis/trans ratio of about 1:7, according to $^1$H-NMR.

The end products of the formula (I)

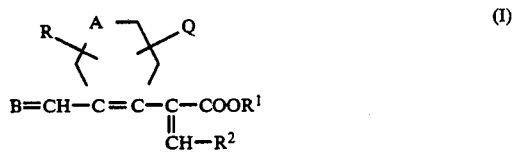

which are listed in Table 2 below are obtained analogously to the process described in Example 1 and taking into consideration the instructions in the descriptions of the processes according to the invention:

TABLE 2

| Ex. No. | R | Q | $R^1$ | $R^2$ | A | B | E/Z[1] | E/Z[2] | physical constants |
|---|---|---|---|---|---|---|---|---|---|
| 2 | H | H | $CH_3$ | $OCH_3$ | $CH_2$ | CH—〈phenyl〉 |  | 1:7 | m.p.: 88–92° C. |
| 3 | H | H | $CH_3$ | $OCH_3$ | $CH_2$ | CH—〈thiazolyl-phenyl〉 | E | E | m.p.: 114–117° C. |

TABLE 2-continued

| Ex. No. | R | Q | R¹ | R² | A | B | E/Z[1] | E/Z[2] | physical constants |
|---|---|---|---|---|---|---|---|---|---|
| 4 | H | H | $CH_3$ | $OCH_3$ | $CH_2$ | CH=C(N=CHS-)phenyl | Z | E | $^1$H-NMR[a] |
| 5 | H | H | $CH_3$ | $OCH_3$ | $CH_2$ | bis-thiazole linked structure with CH₃ | E | E | m.p.: 118–119° C. |
| 6 | H | H | $CH_3$ | $OCH_3$ | $CH_2$ | CH=(2-chloropyridin-5-yl) | E | 1:5 | m.p.: 87–89° C. |
| 7 | H | H | $CH_3$ | $OCH_3$ | $CH_2$ | CH=(2-chloropyridin-5-yl) | Z | 1:5 | m.p.: 105–107° C. |
| 8 | H | H | $CH_3$ | $OCH_3$ | — | CH=C(N=CHS-)phenyl | E | E | m.p.: 105–106° C. |
| 9 | H | H | $CH_3$ | $OCH_3$ | — | CH=C(N=CHS-)(4-F-phenyl) | E | E | $^1$H-NMR[β] |
| 10 | H | H | $CH_3$ | $OCH_3$ | $CH_2-CH_2$ | CH=C(N=CHS-)phenyl | E | E | |
| 11 | H | H | $CH_3$ | $OCH_3$ | — | CH=(3-Cl-phenyl) | E | E | m.p.: 110° C. |

TABLE 2-continued
| Ex. No. | R | Q | R¹ | R² | A | B | E/Z[1] | E/Z[2] | physical constants |
|---|---|---|---|---|---|---|---|---|---|
| 12 | H | H | CH₃ | OCH₃ | — | 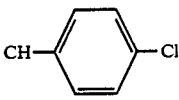 | E | E | δ = 7.50 |
| 13 | H | H | CH₃ | OCH₃ | — | 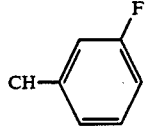 | E | E | m.p.: 100–102° C. |
| 14 | H | H | CH₃ | OCH₃ | — | 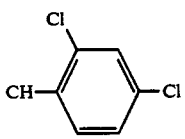 | E | E | m.p.: 56–58° C. |
| 15 | H | H | CH₃ | OCH₃ | — | 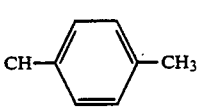 | E | E | δ = 7.45 |
| 16 | H | H | CH₃ | OCH₃ | — | 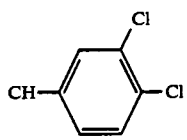 | E | E | m.p.: 86–87° C. |
| 17 | H | H | CH₃ | OCH₃ | — | 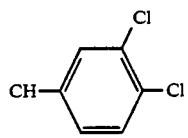 | E | E | m.p.: 74–76° C. |
| 18 | H | H | CH₃ | OCH₃ | — | 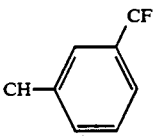 | E | E | m.p.: 76–77° C. |
| 19 | H | H | CH₃ | OCH₃ | — | 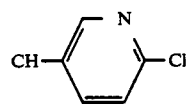 | E | 4:1 | m.p.: 124–127° C. |
| 20 | H | H | CH₃ | OCH₃ | — | 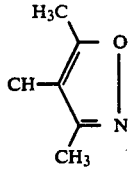 | 5:2 | 4:1 | ms: m/e = 303 |
| 21 | H | H | CH₃ | OCH₃ | — | 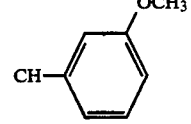 | E | 6:1 | δ = 3.65 |
| 22 | H | H | CH₃ | OCH₃ | — | 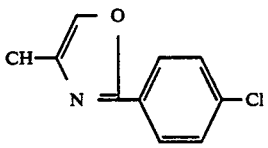 | E | E | ms: m/e = 385 |

TABLE 2-continued

| Ex. No. | R | Q | R¹ | R² | A | B | E/Z[1] | E/Z[2] | physical constants |
|---|---|---|---|---|---|---|---|---|---|
| 23 | H | H | $CH_3$ | $OCH_3$ | — | 1-naphthyl-CH | E | 5:1 | ms: m/e = 334 |
| 24 | H | H | $CH_3$ | $OCH_3$ | — | 3-Br-C₆H₄-CH | E | E | ms: m/e = 364 |
| 25 | H | H | $CH_3$ | $OCH_3$ | — | 3-Cl-4-$OCH_3$-C₆H₃-CH | E | E | ms: m/e = 348 |
| 26 | H | H | $CH_3$ | $OCH_3$ | — | 4-$OCH_3$-C₆H₄-CH | E | E | m.p.: 104–106° C. |
| 27 | H | H | $CH_3$ | $OCH_3$ | — | 4-biphenyl-CH | E | E | m.p.: 162–165° C. |
| 28 | H | H | $CH_3$ | $OCH_3$ | — | 3,5-($OCH_3$)₂-C₆H₃-CH | E | 8:1 | ms: m/e = 344 |
| 29 | H | H | $CH_3$ | $OCH_3$ | — | 2-naphthyl-CH | E | E | ms: m/e = 334 |
| 30 | H | H | $CH_3$ | $OCH_3$ | — | 3-phenoxy-C₆H₄-CH | E | E | ms: m/e = 376 |
| 31 | H | H | $CH_3$ | $OCH_3$ | — | 2,6-Cl₂-C₆H₃-CH | E | E | m.p.: 96–99° C. |
| 32 | H | H | $CH_3$ | $OCH_3$ | — | CH—$C_3H_7$n | E | E | ms: m/e = 250 |
| 33 | H | H | $CH_3$ | $OCH_3$ | — | 3-(O-CH₂-C≡CH)-C₆H₄-CH | | | ms: m/e = 338 |

TABLE 2-continued

| Ex. No. | R | Q | R¹ | R² | A | B | E/Z[1] | E/Z[2] | physical constants |
|---|---|---|---|---|---|---|---|---|---|
| 34 | H | H | CH$_3$ | OCH$_3$ | — | CH—(C$_6$H$_4$)—O—CH$_2$—C$_6$H$_5$ | E | E | δ = 5.05 |
| 35 | H | H | CH$_3$ | OCH$_3$ | — | CH—(C$_6$H$_3$)(OCH$_3$)$_2$ | E | E | m.p.: 108–109° C. |
| 36 | H | H | CH$_3$ | OCH$_3$ | — | CH—(C$_6$H$_4$)—C$_3$H$_7$i | E | E | ms: m/e = 326 |
| 37 | H | H | CH$_3$ | OCH$_3$ | — | CH—(C$_6$H$_4$)—Br | E | E | m.p.: 124–125° C. |
| 38 | H | H | CH$_3$ | OCH$_3$ | — | CH=CH—(C$_6$H$_4$)—N(CH$_3$)$_2$ | E | E | m.p.: 194–196° C. |
| 39 | H | H | CH$_3$ | OCH$_3$ | — | CH—(C$_6$H$_4$)—F | E | E | m.p.: 112–113° C. |
| 40 | H | H | CH$_3$ | OCH$_3$ | — | CH—(C$_6$H$_4$)—NO$_2$ | E | E | ms: m/e = 329 |
| 41 | H | H | CH$_3$ | OCH$_3$ | — | CH—(C$_6$H$_2$)(OCH$_3$)$_3$ | E | E | m.p.: 144–146° C. |
| 42 | H | H | CH$_3$ | OCH$_3$ | — | CH—(C$_6$H$_3$)(OCH$_3$)(F) | E | E | m.p.: 124–125° C. |
| 43 | H | H | CH$_3$ | OCH$_3$ | — | CH—(C$_6$H$_4$)—OCH$_2$—C$_6$H$_5$ | E | E | m.p.: 130–131° C. |
| 44 | H | H | CH$_3$ | OCH$_3$ | — | CH—(methylenedioxyphenyl) | E | E | m.p.: 118–119° C. |
| 45 | H | H | CH$_3$ | OCH$_3$ | — | CH—CH=CH—C$_6$H$_5$ | E | E | m.p.: 76–77° C. |

TABLE 2-continued
| Ex. No. | R | Q | R¹ | R² | A | B | E/Z[1] | E/Z[2] | physical constants |
|---|---|---|---|---|---|---|---|---|---|
| 46 | H | H | CH₃ | OCH₃ | — | 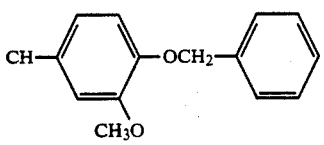 | E | E | m.p.: 98–99° C. |
| 47 | H | H | CH₃ | OCH₃ | — | 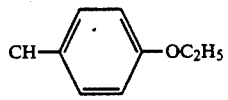 | E | E | m.p.: 114–116° C. |
| 48 | H | H | CH₃ | OCH₃ | — | 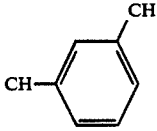 | E | E | m.p.: 72–74° C. |
| 49 | H | H | CH₃ | OCH₃ | — | 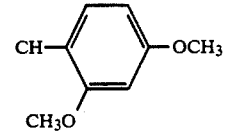 | E | E | δ = 3.65, 3.7 |
| 50 | H | H | CH₃ | OCH₃ | — | 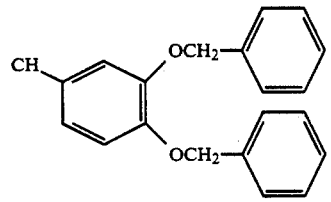 | E | E | m.p.: 121–122° C. |
| 51 | H | H | CH₃ | OCH₃ | — | 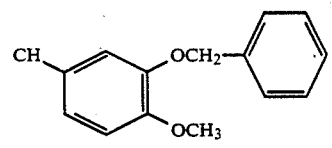 | E | E | m.p.: 64–65° C. |
| 52 | H | H | CH₃ | OCH₃ | CH₂ | 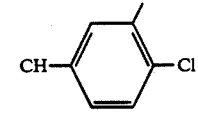 | E | E | m.p.: 80–81° C. |
| 53 | H | H | CH₃ | OCH₃ | CH₂ | 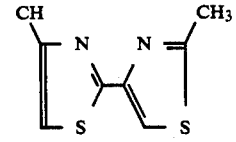 | E | E | m.p.: 122–123° C. |
| 54 | H | H | CH₃ | OCH₃ | CH₂ | 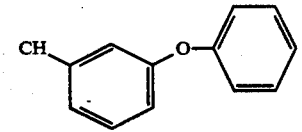 | E | 8:1 | δ = 3.7 |
| 55 | H | H | CH₃ | OCH₃ | O | 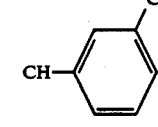 | E | E | δ = 6.2 |

TABLE 2-continued

| Ex. No. | R | Q | R¹ | R² | A | B | E/Z[1] | E/Z[2] | physical constants |
|---------|---|---|-----|------|---|---|--------|--------|---------------------|
| 56 | H | H | CH₃ | OCH₃ | O | CH—⟨phenyl⟩ | E | 12:1 | δ = 6.3 |
| 57 | H | H | CH₃ | OCH₃ | S | CH—⟨phenyl-Cl⟩ | E | 5:1 | Oil |

¹H-NMR-data:
α)(CDCl₃, δ/ppm): δ = 3.75(s, 3H, OCH₃), 3.89(s, 3H, OCH₃), 6.41(s, 1H), 6.58(d, 1H), 7.05(s, 1H), 7.50(d, 1H)
β)(CDCl₃, δ/ppm): δ = 3.75(s, 3H, OCH₃), 3.85(s, 3H, OCH₃), 6.49(d, 1H), 7.03(s, 1H)
\*)The ¹H-NMR spectra were recorded in deuterochloroform (CDCl₃) with tetramethylsilane (TMS) as the internal standard. The chemical shift is indicated as δ value in ppm.
E/Z[1] at double bond with radical R²
E/Z[2] at double bond with radical B

PREPARATION OF THE PRECURSORS

Example (IV-1)

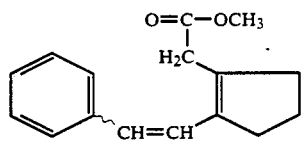

A total of 43.12 g (110.9 mmol) of benzyltriphenylphosphonium chloride are added in portions to a mixture, stirred at 0° C. under argon, of 280 ml of methanol, 140 ml of tetrahydrofuran and 8.12 g (150.1 mmol) of sodium methanolate. Stirring is continued for about 30 minutes, and, after this, a solution of 14.00 g (83.2 mmol) of methyl 2-formyl-cyclopent-1-en-1-yl-acetate in 10 ml of tetrahydrofuran is added dropwise with cooling over a period of about 30 minutes. When the dropwise addition is complete, the mixture is allowed to come to room temperature, and stirring is continued until the reaction is complete. For working up, ice-water is added to the mixture which is then extracted with ethyl acetate, the extract is dried over anhydrous magnesium sulphate and concentrated, and the residue is purified by chromatography on silica gel (eluent: dichloromethane).

This gives 10.50 g (52.1% of theory) of methyl 1-(2-phenyl-ethenyl)-2-cyclopenteneacetate having a cis-/trans ratio of 1:3 as determined by ¹H-NMR and a purity of 95.4%, according to GC.

¹H-NMR (CDCl₃, δ/ppm): 3.62 (s, 3H, COOCH₃/cis-isomer), 3.70 (s, 3H, COOCH₃/trans-isomer, 6.22 (d, 1H, CH═/cis-isomer), 6.48 (d, 1H, CH═/trans-isomer), 6.51 (d, 1H, CH═/cis-isomer), 7.03 (d, 1H, CH═/trans-isomer); I$_{CH═CH(cis)}$=12.1 Hz, I$_{CH═CH(trans)}$=15.9 Hz.

The precursors of the formula (IV)

(IV)

which are listed in Table 3 below are obtained analogously to Example (IV-1) and taking into consideration the instructions in the descriptions of the processes according to the invention.

TABLE 3

| Ex. No. | R | Q | R¹ | A | B | cis/trans | Physical constants (mass spectroscopy) |
|---------|---|---|-----|---|---|-----------|----------------------------------------|
| IV-2 | H | H | CH₃ | — | CH═⟨thiazole-phenyl⟩ | trans | MS: 326(M⊕), 252(base peak) |
| IV-3 | H | H | CH₃ | — | CH═⟨thiazole-phenyl-F⟩ | trans | MS: 343(M⊕), 270(base peak) 193 |
| IV-4 | H | H | CH₃ | — | CH═⟨thiazole-phenyl-OCH₃⟩ | trans | MS: 339(M⊕), 266(base peak) 189, 135 |

TABLE 3-continued

| Ex. No. | R | Q | $R^1$ | A | B | cis/trans | Physical constants (mass spectroscopy) |
|---|---|---|---|---|---|---|---|
| IV-5 | H | H | $CH_3$ | — | (thiazole-linked bis-thiazole structure with $CH_3$) | trans | MS: 343($M^\oplus$), 313, 273(base peak) |
| IV-6 | H | H | $CH_3$ | $CH_2$ | HC—phenyl | 32:1 | MS: 256($M^\oplus$) und (base peak) |
| IV-7 | H | H | $CH_3$ | $CH_2$ | CH—pyridine—Cl | 5:3 | MS: 291/293($M^\oplus$), 258, 232, 202 |
| IV-8 | H | H | $CH_3$ | $CH_2$ | CH—thiazole—phenyl | trans | MS: 339($M^\oplus$) |
| IV-9 | H | H | $CH_3$ | $CH_2$ | (thiazole-linked bis-thiazole structure with $CH_3$) | trans | MS: 360($M^\oplus$), 287(base peak), 218, 142 |
| IV-10 | H | H | $CH_3$ | $CH_2CH_2$ | CH—thiazole—phenyl | trans | MS: 353($M^\oplus$), 280(base peak), 179, 121 |

Example (IX-1)

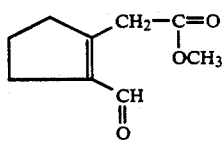

A mixture of 29.0 g (0.1 mol) of methyl 2-(benzoyl-methylene)-1-cyclopentanol acetate, 300 cm³ of ether and 150 cm³ of a 33% strength aqueous sulphuric acid is stirred vigorously until the reaction is complete. The organic phase is separated off and extracted with ether. The combined extracts are washed with saturated sodium chloride solution, saturated sodium carbonate solution (until the reaction of the wash solution is clearly alkaline) and again with sodium chloride solution, dried over anhydrous magnesium sulphate and concentrated.

This gives 14.1 g (83.8% of theory) of methyl (2-formylcyclopent-1-en-1-yl)acetate.

Example (XI-2)

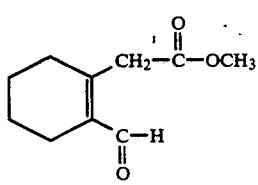

Methyl (2-formyl-cyclohex-1-en-1-yl)acetate is obtained analogously to Example (XI-1) in a yield of 75% of theory.

PREPARATION OF THE STARTING MATERIALS

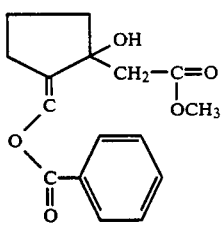

A stirred mixture of 43.00 g (198.9 mmol) of 2-(benzoyloxy-methylene)-cyclopentanone, 72.28 g (472.5 mmol) of methyl bromoacetate, 62.24 g (958.2 mmol) of zinc powder and 400 cm³ of ether is refluxed with ultrasonic treatment until the reaction is complete.

For working up, the mixture is allowed to cool, and a solution of 25 cm³ of acetic acid in 100 ml of ether is added carefully, stirring is continued for 15 minutes, and the mixture is rendered neutral by stirring it with a suspension of excess sodium hydrogen carbonate in a little water. The ether phase is decanted off, and the aqueous suspension of the zinc residues is extracted repeatedly and thoroughly with ethyl acetate.

The combined organic solutions are dried over anhydrous magnesium sulphate and concentrated. The crystalline residue is suspended in diisopropyl ether, filtered off with suction and dried under reduced pressure. More product crystallizes from the mother liquor.

This gives 29.9 g (52% of theory) of methyl 2-(benzoyloxymethylene)-1-cyclopentanolacetate of melting point m.p.: 69°-70° C.

Methyl 2-(benzoyloxy-methylene)-1-cyclohexanolacetate of melting point m.p.: 92°-94° C. is obtained analogously (yield: 64% of theory).

Methyl 2-(benzoyloxy-methylene)-1-cycloheptanolacetate is obtained analogously (yield: 59.8% of theory).

General procedure for the benzoylation of the hydroxymethylenecycloalkanones A solution of 35.14 g (0.25 mol) of benzoyl chloride in 100 cm³ of ether is added dropwise at 0°-10° C. to a mixture of 0.250 mol of the hydroxymethylenecycloalkanone, 21.75 g (0.275 mol) of pyridine and 250 cm³ of ether, with stirring. When the addition is complete, stirring is continued at room temperature for 3-4 hours, the mixture is then heated to reflux and filtered while warm. The residue which remains is extracted by repeatedly suspending it in warm ether and filtering off the solutions, and the combined organic solutions are evaporated to dryness. The residue which remains is suspended in diisopropyl ether and filtered off with suction.

The following are obtained in this manner, 2-(benzoyl-methylene)-cyclopentanone of melting point m.p.: 75°-77° C. (yield 80.6% of theory), 2-(benzoylmethylene)cyclohexanone of melting point m.p.: 91°-92° C. (yield 80% of theory) and 2-(benzoylmethylene)-cycloheptanone of melting point m.p.: 102°-104° C. (yield: 77.2% of theory).

General procedure for the preparation of oxymethylenecycloalkanes 1.02 mol of sodium hydride (in the form of a suspension) are added in portions with stirring and at room temperature to a mixture of 1.02 mol of the ketone, 76.0 g of ethyl formate and 800 cm³ of ether. In the beginning, it is frequently necessary to heat the mixture to reflux once the reaction has started, it may necessary to apply external cooling. The reaction mixture, which eventually solidifies, is allowed to stand overnight at room temperature.

For working up, ice-water is added (about 500 ml), the organic phase is separated off, and the aqueous solution is washed with 250 cm³ of ether. 60 g of acetic acid are added to the aqueous phase which remains, and the mixture is extracted repeatedly with ether. The combined extracts are dried over magnesium sulphate, filtered and concentrated, and the residue is distilled under reduced pressure.

The following are obtained in this manner:
oxymethylenecyclopentanone b.p.$_{12-14}$ 78°-84° C. (yield: 30% of theory),
oxymethylenecyclohexanone b.p.$_{12-14}$ 80°-84° C. (yield: 58% of theory) and
oxymethylenecycloheptanone b.p.$_{12-14}$ 82°-88° C. (yield: 43.6% of theory).

Use Examples

In the Use Examples which follow, the compound listed below was employed as comparison substance:

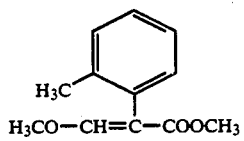

(A)

methyl 3-methoxy-2-(2-methylphenyl)-acrylate (disclosed in EP 178,816)

EXAMPLE A

Venturia test (apple)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to Preparation Examples 1 and 2.

EXAMPLE B

Pyricularia test (rice)/protective

Solvent: 12.5 parts by weight of acetone

Emulsifier: 0.3 parts by weight of alkylaryl polyglycol ether

To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to Preparation Examples 1, 2 and 3.

EXAMPLE C

Erysiphe Test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores and *Erysiphe graminis* f. sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compound according to Preparation Example (1).

EXAMPLE D

Erysiphe Test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f. sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to Preparation Examples (1) and (2).

EXAMPLE E

Leptosphaeria nodorum-test (wheat)/protective

Solvent: 100 parts by weight of dimethylformamide
Emulsifer: 0.25 parts by weight of alylaryl polyglycolether To produce a suitable preparation of active compound, 1 part by weight of active compound is mixed with the stated amounts of solvent and emulsifer, and the concentrate is diluted with water to the desired concentration.

To test for protective activity, young plants are sprayed with the preparation of active compound until dew-moist. After the spray coating has dried on, the plants are sprayed with a conidium suspension of *Leptosphaeria nodorum*. The plants remain in an incubation cabin at 20° C. and 100% relative atmospheric humidity for 48 hours.

The plants are placed in a greenhouse at a temperature of about 15° C. and a relative atmospheric humidity of about 80%.

Evaluation is carried out 10 days after the inoculation.

In this test, a clearly superior activity compared with the prior art is shown, for example, by the compounds according to Preparation Examples (8) and (9).

EXAMPLE F

Cochliobolus sativus-test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifer, and the concentrate is diluted with water to the desired concentration.

To test for protective activity, young plants are sprayed with the preparation of active compound until dew-moist. After the spray coating has dried on, the plants are sprayed with a conidium suspension of *Cochliobolus sativus*. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to Preparation Examples (1), (8) and (9).

EXAMPLE G

Pyrenophora teres test (barley)/protective

Solvent: 100 parts by weight dimethylformamide
Emulsifier: 0.25 parts by weight alkylarylpolyglycol ether To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound until dew-moist. After the spray coating has dried off, the plants are sprayed with a conidium suspension of

*Pyrenophora teres.* The plants then remain in an incubation cabin at 20° C. and 100% relative atmospheric humidity for 48 hours.

The plants are placed in a greenhouse at a temperature of about 20° C. and a relative atmospheric humidity of about 80°.

Evaluation is carried out 7 days after the inoculation.

In this test, a clearly superior activity compared with the prior art is shown, for example, by the compounds according to Preparation Example (1), (2), (3), (5) and (8).

It will be understood that the specification and examples are illustrative but not limitative of the present invention and that other embodiments within the spirit and scope of the invention will suggest themselves to those skilled in the art.

We claim:

1. An acrylic ester of the formula

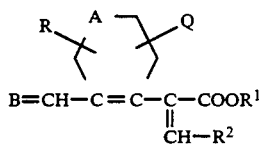

in which $R^1$ represents alkyl, or represents unsubstituted or substituted aralkyl, unsubstituted or substituted aryl are those as defined in $R^8$ $R^2$ represents dialkylamino, or represents a radical —Z—$R^3$, $R^3$ represents alkyl, or represents unsubstituted or substituted aralkyl, Z represents oxygen or sulphur, A represents

where n represents a number from 0 to 6, $R^4$ and $R^5$ in each case independently of one another represent alkyl, or together represent an alkylene chain having 2 to 7 carbon atoms, and $R^6$ represents alkyl, or represents a radical

where $R^7$ represents alkyl, alkoxy or dialkylamino,

B represents the group CH—$R^8$, where $R^8$ represents unsubstituted or substituted aryl and R and Q independently of one another represent hydrogen, alkyl, halogenoalkyl or alkoxy.

2. An acrylic ester according to claim 1, in which $R^1$ represents straight-chain or branched alkyl having 1 to 6 carbon atoms, or represents aralkyl which has 1 to 4 carbon atoms in the straight-chain or branched alkyl moiety and 6 to 10 carbon atoms in the aryl moiety and which is unsubstituted or monosubstituted or polysubstituted in the aryl moiety by identical or different substituents, the aryl substituents being those mentioned in the case of $R^8$ hereinbelow, $R^2$ represents dialkylamino having 1 to 6 carbon atoms in each of the individual straight-chain or branched alkyl moieties, or represents a radical —Z—$R^3$, where $R^3$ represents straight-chain or branched alkyl having 1 to 6 carbon atoms, or represents aralkyl which has 1 to 4 carbon atoms in the straight-chain or branched alkyl moiety and 6 to 10 carbon atoms in the aryl moiety and which is unsubstituted or monosubstituted or polysubstituted in the aryl moiety by identical or different substituents, the aryl substituents being those mentioned in the case of $R^8$ hereinbelow, Z represents oxygen or sulphur, A represents

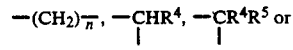

where n represents a number from 0 to 3, $R^4$ and $R^5$ in each case independently of one another represent straight-chain or branched alkyl having 1 to 6 carbon atoms, or together represent an alkylene chain having 2 to 7 carbon atoms, and $R^6$ represents straight-chain or branched alkyl having 1 to 6 carbon atoms, or represents a radical

where $R^7$ represents straight-chain or branched alkyl having 1 to 6 carbon atoms, straight-chain or branched alkoxy having 1 to 6 carbon atoms, or straight-chain or branched dialkylamino having 1 to 6 carbon atoms in each of the individual alkyl moieties, B represents the group CH—$R^8$, where $R^8$ represents unsubstituted or substituted aryl having 6 to 10 carbon atoms in the aryl moiety, the substituents in each case being selected from the group consisting of halogen, cyano, nitro, in each case straight-chain or branched alkyl, alkoxy or alkylthio, each of which has 1 to 4 carbon atoms, alkylidenedioxy having 1 to 6 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, cycloalkyl having 3 to 7 carbon atoms, divalent alkanediyl having 3 to 5 carbon atoms, or aryl, aralkyl, aryloxy, arylthio, aralkyloxy or aralkylthio, each of which has 6 to 10 carbon atoms in the aryl moiety and where appropriate 1 to 4 carbon atoms in the straight-chain or branched alkyl moiety and each of which is optionally monosubstituted or polysubstituted in the aryl moiety by identical or different substituents from the group consisting of halogen, alkyl, alkoxy, alkylthio, halogenoalkyl, halogenoalkoxy and halogenoalkylthio, each of which has 1 to 4 carbon toms and if appropriate 1 to 9 identical or different halogen atoms, R and Q independently of one another represent hydrogen, alkyl having 1 to 4 carbon atoms, alkoxy having 1 to 4 carbon atoms or halogenoalkyl having 1 to 4 carbon atoms and 1 to 9 identical or different halogen atoms.

3. An acrylic ester according to claim 1, in which $R^1$ represents methyl, ethyl, n- or i-propyl or n-, i-, s- or t-butyl, or represents benzyl which is optionally monosubstituted to trisubstituted by identical or different substituents, the substituents being those mentioned in the case of $R^8$, $R^2$ represents dialkylamino having 1 to 4 carbon atoms in each of the individual straight-chain or branched alkyl moieties, or represents a radical $-Z-R^3$, where $R^3$ represents methyl, ethyl, n- or i-propyl or n-, i-, s- or t-butyl, or represents benzyl which is optionally monosubstituted to trisubstituted by identical or different substituents, the substituents being those mentioned in the case of $R^8$, and Z represents oxygen or sulphur;

A represents $-(CH_2)_{\overline{n}}, -CHR^4, -CR^4R^5$ or

where n represents the number 0, 1, 2 or 3, $R^4$ and $R^5$ in each case independently of one another represent straight-chain or branched alkyl having 1 to 4 carbon atoms, or together represent an alkylene chain having 2 to 5 carbon atoms, and $R^2$ represents straight-chain or branched alkyl having 1 to 4 carbon atoms, or represents a radical $-C-R^7$
$\parallel$
$O$ where $R^7$ represents straight-chain or branched alkyl having 1 to 4 carbon atoms, straight-chain or branched alkoxy having 1 to 4 carbon atoms, or straight-chain or branched dialkylamino having 1 to 4 carbon atoms in each of the individual alkyl radicals, B represents the group $CH-R^8$, where $R^8$ represents phenyl, naphthyl, in each case unsubstituted or in each case monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, methylenedioxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoximinoethyl, cyclopentyl, cyclohexyl, 1,3-propanediyl or 1,4-butanediyl, and R and Q independently of one another represent hydrogen, methyl, ethyl, n- or i-propyl, methoxy, ethoxy or halogenoalkyl having 1 or 2 carbon atoms and 1 to 5 identical or different fluorine or chlorine atoms.

4. An acrylic ester according to claim 1, in which $R^1$ represents methyl, ethyl or optionally substituted benzyl, the benzyl substituents being those mentioned in the case of $R^8$;

$R^2$ represents dimethylamino or diethylamino, or represents a radical $-Z-R^3$, where $R^3$ represents methyl, ethyl, n- or i-propyl or benzyl, Z represents oxygen or sulphur;

A represents

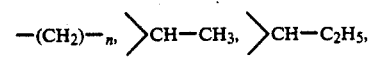

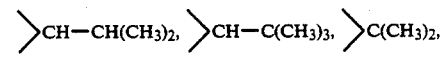

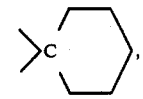

where n represents the number 0, 1, 2 or 3,

B represents the group $CH-R^8$, where $R^8$ represents phenyl, naphthyl, in each case unsubstituted or in each case monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, methylenedioxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoximinoethyl, cyclopentyl, cyclohexyl, 1,3-propanediyl, 1,4-butanediyl, and phenyl, phenoxy, benzyl, benzyloxy, phenylthio and benzylthio, each of which is optionally monosubstituted or disubstituted by identical or different substituents from the group consisting of fluorine, chlorine, bromine, methyl and ethyl;

and R and Q independently of one another represent hydrogen or methyl.

5. An acrylic ester according to claim 1, in which $R^1$ represents methyl or ethyl, $R^2$ represents methoxy, ethoxy, methylthio or dimethylamino, A represents

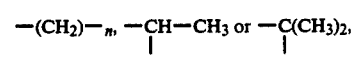

where n represents the number 0, 1 or 2,

B represents the group $CH-R^8$, where $R^8$ represents phenyl, naphthyl, each of which is unsubstituted, monosubstituted to trisubstituted by identical or different substituents selected from the group consisting of fluorine, chlorine, bromine, cyano, nitro, methyl, ethyl, methoxy, ethoxy, methylenedioxy, methylthio, trifluoromethyl, methoxycarbonyl, ethoxycarbonyl, cyclopentyl, cyclohexyl, phenoxy, phenylthio, benzyloxy and benzylthio; and R and Q represent hydrogen.

6. A compound according to claim 1, wherein such compound is methyl E-3-methoxy-2-[2-(2-phenyl-ethenyl)cyclopenten-1-yl]acrylate of the formula

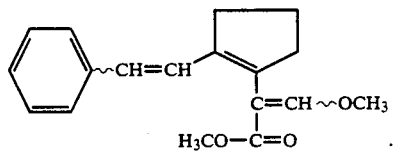

7. A compound according to claim 1, wherein such compound is methyl 3-methoxy-2-[2-(2-phenyl-ethenyl)cyclohexen-1-yl)acrylate of the formula

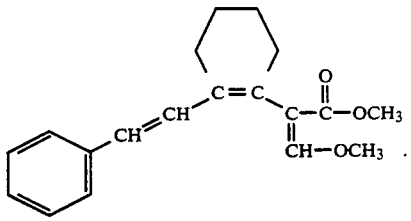

8. An acrylic ester according to claim 1, in which
A represents —(CH$_2$)—$_n$,
n represents 0, and
B represents phenyl —CH or naphthyl —CH.

9. A pesticidal composition comprising a pesticidally effective amount of a compound according to claim 1 and a diluent.

10. A method of combating pests which comprises applying to such pests or to a locus from which it is desired to exclude such pests a pesticidally effective amount of a compound according to claim 1.

11. The method according to claim 10, wherein the hydroxyacrylic ester is selected from the group consisting of
methyl E-3-methoxy-2-[2-(2-phenyl-ethenyl)cyclopenten-1-yl]acrylate,
methyl 3-methoxy-2-[2-(2-phenyl-ethenyl)cyclohexen-1-yl]acrylate and
methyl 3-methoxy-2-[2-(2-(2-phenylthyozol-4-yl)ethenyl)-cyclohexen-1-yl]acrylate.

* * * * *